US 8,206,304 B1

(12) United States Patent
Douglas et al.

(10) Patent No.: US 8,206,304 B1
(45) Date of Patent: Jun. 26, 2012

(54) DOPPLER TRANSCEIVER AND PROBE FOR USE IN MINIMALLY INVASIVE PROCEDURES

(75) Inventors: Gary Douglas, Billerica, MA (US); David Regan, Pelham, NH (US); Nilendu Srivastava, Chelmsford, MA (US); Rachana Suchdev, Nashua, NH (US)

(73) Assignee: Vascular Technology Incorporated, Nashua, NH (US)

( * ) Notice: Subject to any disclaimer, the term of this patent is extended or adjusted under 35 U.S.C. 154(b) by 721 days.

(21) Appl. No.: 11/014,037

(22) Filed: Dec. 16, 2004

Related U.S. Application Data

(60) Provisional application No. 60/529,779, filed on Dec. 16, 2003.

(51) Int. Cl.
*A61B 8/14* (2006.01)
(52) U.S. Cl. ................ 600/459; 600/453; 600/455
(58) Field of Classification Search .......... 600/407–410, 600/437–468; 601/2–4
See application file for complete search history.

(56) References Cited

U.S. PATENT DOCUMENTS

| | | | | |
|---|---|---|---|---|
| 4,582,067 A * | 4/1986 | Silverstein et al. | ........... | 600/455 |
| 4,671,292 A * | 6/1987 | Matzuk | ........... | 600/445 |
| 4,967,753 A * | 11/1990 | Haase et al. | ........... | 600/468 |
| 5,040,537 A * | 8/1991 | Katakura | ........... | 600/431 |
| 5,052,395 A * | 10/1991 | Burton et al. | ........... | 600/455 |
| 5,054,491 A | 10/1991 | Saito et al. | | |
| 5,174,295 A * | 12/1992 | Christian et al. | ........... | 600/468 |
| 5,178,150 A * | 1/1993 | Silverstein et al. | ........... | 600/463 |
| 5,394,878 A * | 3/1995 | Frazin et al. | ........... | 600/462 |
| 5,443,072 A * | 8/1995 | Kagan et al. | ........... | 600/504 |
| 5,514,146 A | 5/1996 | Lam et al. | | |
| 5,588,434 A | 12/1996 | Fujimoto | | |
| 5,680,865 A * | 10/1997 | Tanaka | ........... | 600/441 |
| 5,938,615 A * | 8/1999 | Eberle et al. | ........... | 600/463 |
| 6,004,269 A * | 12/1999 | Crowley et al. | ........... | 600/439 |
| 6,102,867 A * | 8/2000 | Dietz et al. | ........... | 600/461 |
| 6,217,519 B1 * | 4/2001 | Grund et al. | ........... | 600/463 |
| 6,344,024 B1 * | 2/2002 | Brucher et al. | ........... | 600/459 |
| 6,425,866 B1 | 7/2002 | Brucher et al. | | |
| 6,546,934 B1 * | 4/2003 | Ingle et al. | ........... | 128/898 |
| 6,582,370 B2 * | 6/2003 | Jibiki | ........... | 600/455 |
| 6,641,536 B2 * | 11/2003 | Hossack et al. | ........... | 600/443 |
| 6,964,640 B2 * | 11/2005 | Zumeris et al. | ........... | 600/459 |
| 6,969,352 B2 * | 11/2005 | Chiang et al. | ........... | 600/437 |

(Continued)

OTHER PUBLICATIONS

Wong Richard, "Endoscopic Doppler US probe for acute peptic ulcer hemorrhage", Gastrointestinal Endoscopy., Nov. 2004, pp. 804-812, vol. 60, No. 5.

(Continued)

*Primary Examiner* — Sanjay Cattungal
(74) *Attorney, Agent, or Firm* — Maine Cernota & Rardin

(57) ABSTRACT

A system is disclosed for the detection of blood flow. The system provides, a portable transceiver unit having a signal generator, a signal comparator, and an audio output whereby a user receives an audio signal indicating differences in Doppler signal, and a Doppler probe coupled to the portable transceiver. The Doppler probe including a piezoelectric crystal disposed at a first end of the Doppler probe; at least one wire transmitting signals between the transceiver unit to the piezoelectric crystal; a rigid or flexible sheath disposed around at least part of the at least one wire and the piezoelectric crystal; and a transceiver unit coupler disposed at a second end of the Doppler probe. The system may also have a quantitative blood flow meter or signal strength meter.

25 Claims, 14 Drawing Sheets

U.S. PATENT DOCUMENTS

| | | | | |
|---|---|---|---|---|
| 7,473,224 | B2 * | 1/2009 | Makin | 600/439 |
| 2003/0153831 | A1 * | 8/2003 | Zumeris et al. | 600/437 |
| 2004/0138563 | A1 * | 7/2004 | Moehring et al. | 600/439 |

OTHER PUBLICATIONS

Kohler, Bernd et al., "Endoscopic Doppler US", Gastrointestinal Endoscopy, Sep. 2004, pp. 493-495, vol. 60, No. 3.

Jakobs, Ralf et al., "Endoscopic Doppler Ultrasound after Injection Therapy for Peptic Ulcer Hemorrhage", Hepato-Gastroenterology, Jul.-Aug. 2004, pp. 1206-1209, vol. 51, No. 58.

Huang, Christopher et al., "Nonvariceal uppter gastrointestinal bleeding", Gastroenterology Clinics of North Amercia, Dec. 2003, pp. 1053-1078, vol. 32, No. 4.

Van Leerdam, Monique et al., "The role of endoscopic Doppler US in patients with peptic ulcer bleeding", Gastrointestinal Endoscopy, Nov. 2003, pp. 677-684, vol. 58, No. 5.

Battaglia, Giorgio et al., "Endoscopic Doppler US-guided injection therapy for gastric varices: case report", Gastrointestinal Endoscopy, Apr. 2003, pp. 608-611, vol. 57, No. 4.

Sandhu, Iqbal et al., "Gastrointestinal endoscopic ultrasonography", Medical Clinics of North America, Nov. 2002, pp. 1289-1317, vol. 86, No. 6.

Pedersen, Finn et al., "Gastric arteriovenous malformation: Doppler EUS-guided diagnosis and therapy", Gastrointestinal Endoscopy, Apr. 2002, pp. 597-599, vol. 55, No. 4.

Bhasin, D.K. et al. "Variceal Bleeding and Portal Hypertension: Much to Learn, Much to Explore", Endoscopy, Feb. 2002, pp. 119-128, vol. 34, No. 2.

Rollhauser, C. et al., "Nonvariceal Upper Gastrointestinal Bleeding", Endoscopy, Feb. 2002, pp. 111-118, vol. 34, No. 2.

Wong, Richard et al., "Visualization of subsurface blood vessels by color Doppler optical coherence tomography in rats: before and after hemostatic therapy", Gastrointestinal Endoscopy, Jan. 2002, pp. 88-95, vol. 55, No. 1.

Folvik, G. et al., "Endosconography-Guided Endoscopic Band Ligation of Dieulafoy's Malformation: A Case Report", Endoscopy, Jul. 2001, pp. 636-638, vol. 33, No. 7.

Norton, Ian et al., "Initial experience with steerable, phased vector array ultrasound catheter in the GI tract", Gastrointestinal Endoscopy, Apr. 2001, pp. 496-499, vol. 53, No. 4.

Lee, John et al., "Recurrent ulcer bleeding: is the hemoclip an answer?", Gastrointestinal Endoscopy, Feb. 2001, pp. 256-258, vol. 53, No. 2.

Gostout, Christopher, "Do we need more technology to reduce recurrence of bleeding from ulcers?", Gastrointestinal Endoscopy, Sep. 2000, pp. 438-440, vol. 52, No. 3.

Wong, Richard et al., "Role of Doppler US in acute peptic ulcer hemorrhage: can it predict failure of endoscopic therapy?", Gastrointestinal Endoscopy, Sep. 2000, pp. 315-321, vol. 52, No. 3.

Riemann, Jurgen et al., "The role of Doppler ultrasound in gastrointestinal bleeding.", Bailliere's Clinical Gastroenterology, Jun. 2000, pp. 495-504, vol. 14, No. 3.

Freeman, Martin, "Value of stigmata in decision-making in gastrointestinal hemmorrhage.", Bailliere's Clinical Gastroenterology, Jun. 2000, pp. 411-425, vol. 14, No. 3.

Lahoti, Sandeep et al., "Obliteration of esophageal varices using EUS-guided sclerotherapy with color Doppler", Gastrointestinal Endoscopy, Mar. 2000, pp. 331-333, vol. 51, No. 3.

Sivak Jr., Michael, "Endoscopic technology: Is this a good as it gets?", Gastrointestinal Endoscopy, Nov. 1999, pp. 718-721, vol. 50, No. 5.

Kohler, Bernd et al., "The Role of Endoscopic Doppler-Sonography.", Hepato-Gastroenterology, Mar.-Apr. 1999, pp. 732-736, vol. 46, No. 26.

Jensen, Dennis, "Management of Sever Ulcer Rebleeding.", New England Journal of Medicine, Mar. 11, 1999, pp. 799-801, vol. 340, No. 10.

Amaro, Rafael et al., "Acute ulcer bleeding: a prospective randomized trail to compare Doppler and Forrest classifications in endoscopic diagnosis and therapy.", Gastrointestinal Endoscopy, May 1998, pp. 426-427, vol. 47, No. 5.

Nesje, L.B. et al., "Dieulafoy's Vascular Malformation: Role of Endoscopic Ultrasonographyn in Therapeutic Decision-Making.", Scand J Gastroenterol, Jan. 1998, pp. 103-108, vol. 33, No. 1.

Kohler, Bernd et al., "Acute Ulcer Bleeding. A Prospective Randomized Trial to Compare Doppler and Forrest Classifications in Endoscopic Diagnosis and Therapy.", Digestive Disease and Sciences, Jul. 1997, pp. 1370-1374, vol. 42, No. 7.

Jiranek, Geoffrey et al., "A Cost-Effective Approach to the Patient With Peptic Ulcer Bleeding", Surgical Clinics of North America, Feb. 1996, pp. 83-103, vol. 76, No. 1.

Jaspersen, D. et al., "Diagnosis and Treatment Control of Bleeding Intestinal Angiodysplasias with and Endoscopic Doppler Device.", Bildgebung, Mar. 1995, pp. 14-17, vol. 62, No. 1.

Kohler, B. et al., "Does Doppler Ultrasound Improve the Prognosis of Acute Ulcer Bleeding?", Hepato-Gastroenterology, Feb. 1994, pp. 51-53, vol. 41, No. 1.

Jaspersen, Daniel et al., "Diagnosis and treatment control of bleeding colorectal angiodysplasias by endoscopic Doppler sonography: a preliminary study.", Gastrointestinal Endoscopy, Jan.-Feb. 1994, pp. 40-44, vol. 40, No. 1.

Jaspersen, D., "Dieulafoy's disease controlled by Doppler ultrasound endoscopic treatment.", Gut, Jun. 1993, pp. 857-858, vol. 34, No. 6.

Silverstein, F., "Ulcer Bleeding Stigmata: What is Better than the Endoscopist's eye?", Endoscopy, Mar. 1993, pp. 246-247, vol. 25, No. 3.

Kohler, B. et al., "Endoscopic Injection Therapy of Forrest II and Forrest III Gastroduodenal Ulcers Guided by Endoscopic Doppler Ultrasound.", Endoscopy, Mar. 1993, pp. 219-233, vol. 25, No. 3.

Jaspersen, D. et al., "Endoscopic Doppler Sonography in gastroduodenal ulcer bleeding.", Clinical Investigator, Aug. 1992, pp. 705, vol. 70, No. 8.

Miller, L.S. et al., "The Endoscopic Doppler and Ulcer Rebleeding Risk: Probing the Source", Gastroenterology, Feb. 1992, pp. 734-736, vol. 102, No. 2.

Kohler, B. et al., "The endoscopic Doppler: Its Value in Evaluating Gastroduodenal Ulcers after Hemorrhage and as an Instrument of Control of Endoscopic Injection Therapy.", Scand J Gastroenterol, May 1991, pp. 471-476, vol. 26, No. 5.

Rutgeerts, P. et al., "Transendoscopic Doppler Ultrasound: Usefulness for Diagnosis and Treatment of Vascular Malformations.", Endoscopy, May 1988, pp. 99-101, vol. 20, No. 3.

Fullarton, G.M. et al., "Prediction of Rebleeding in Peptic Ulcers by Visual Stigmata and Endoscopic Doppler Ultrasound Criteria.", Endoscopy, Mar. 1990, pp. 68-71, vol. 22, No. 2.

Schmitt, W. et al., "Colonic Haemorrhage from Solitary Submucosal Vessels Diagnosed by Lower Gastrointestinal Doppler-Endoscopy.", Endoscopy, Jan. 1987, pp. 43-45, vol. 19, No. 1.

Silverstein, F.E. et al., "An Endoscopic Doppler Probe: Preliminary Clinical Evaluation", Ultrasound in Med. & Biol., Mar.-Apr. 1985, pp. 347-353, vol. 11, No. 2.

Martin, Roy et al., "An Endoscopic Doppler Probe for Assessing Intestinal Vasculature", Ultrasound in Med. & Biol., Jan.-Feb. 1985, pp. 61-69, vol. 11, No. 1.

Beckly, D.E. et al., "The Use of Doppler Ultrasound Probe for Localising Arterial Blood Flow during Upper Gastrointestinal Endoscopy.", Endoscopy, Jul. 1982, pp. 146-147, vol. 14, No. 4.

Parsons, J. et al., "Complications of Abdominal Urologic Laparoscopy: Longitudinal Five-Year Analysis.", Urology, Jan. 2004, pp. 27-32, vol. 63, No. 1.

Martay, Kenneth et al., "Unexpected surgical difficulties leading to hemorrhage and gas embolus during laparoscopic donor nephrectomy: a case report.", Canadian Journal of Anesthesia, Nov. 2003, pp. 891-894, vol. 50, No. 9.

Hsu, Thomas et al., "Renovascular Complications of Laparoscopic Donor Nephrectomy", Urology, Nov. 2002, pp. 811-815, vol. 60, No. 5.

Menon, Mani et al., "Laparoscopic and Robot Assisted Radical Prostatectomy: Establishment of a Structured Program and Preliminary Analysis of Outcomes", The Journal of Urology, Sep. 2002, pp. 945-949, vol. 168, No. 3.

Troppmann, Christoph et al., "Increased Transplantation of Kidneys with Multiple Renal Arteries in the Laproscopic Liver Donor Nephrectomy Era", Arch Surg., Aug. 2001, pp. 897-907, vol. 136, No. 8.

Beckly, D.E. et al., "Prediction of rebleeding from peptic ulcer experience with an endoscopic Doppler device", Gut, Jan. 1986, pp. 96-99, vol. 27, No. 1.

Cadeddu, Jeffrey et al., "Laparoscopic Radical Prostatectomy: Is It Feasible and Reasonalbe?", Radical Prostatectomy, Aug. 2001, pp. 655-661, vol. 28, No. 3.

Breda, Guglielmo et al., "Future Developments and Perspectives in Laparoscopy", European Urology, Jan. 2001, pp. 84-91, vol. 40, No. 1.

Janetschek, Gunter, "Laparoscopic Retroperitoneal Lymph Node Dissection", Urologic Clinics of North America, Feb. 2001, pp. 107-114, vol. 28, No. 1.

Gill, Inderbir, "Needlescopic Urology: Current Status", Urologic Clinics of North America, Feb. 2001, pp. 71-83, vol. 28, No. 1.

Das, Sakti, "Urologic Laparascopy: The Future Is Now", Urologic Clinics of North America, Feb. 2001, pp. 1-3, vol. 28, No. 1.

Gill, Inderbir et al., "Advances in Urological Laparascopy", American Urologic Assoc., Oct. 1995, pp. 1275-1294, vol. 154, No. 4.

Pollak, Raymond et al., "Anatomic Abnormalities of Cadaver Kidneys Procured for Purposes of Transplantation", The American Surgeon, May 1986, pp. 233-235, vol. 52, No. 5.

"The Endoscopic Doppler Device", [online] [retrieved on Jun. 3, 2002] Retrieved from the internet <URL:hppt://www.dwl.de/systems/endo/endo.html>, pp. 1-2.

Jaspersen, D. et al., "Doppler controlled diagnosis and treatment of gastrointestinal angiodysplasi", Gastroenterol Jpn., Aug. 1993, pp. 491-495, vol. 28, No. 3. (Abstract Only).

Jaspersen, D. et al., "Doppler-controlled injection treatment of Dieulafoy's disease", J Gastroenterol Hepatol, May-Jun. 1993, pp. 267-269, vol. 8, No. 3. (Abstract Only).

Kohler, B. et al., "Significance of the ulcer vessel in acute ulcer hemorrhage—value of local endoscopic therapy in combination with endoscopic Doppler ultrasound", Z Gastroenterol, Jul. 1992, pp. 481-485, vol. 30, No. 7. (Abstract Only).

Jaspersen, D., "Endoscopic Doppler ultrasound in gastroduodenal ulcer hemorrhage", Fortschr Med., Jun. 1992, pp. 336-339, vol. 110, No. 18. (Abstract Only).

Jaspersen, D., "Endoscopic Doppler ultrasonography in lower intestinal bleeding: vascular diagnosis and monitoring of therapy", Schweiz Med Wochenschr, May 1992, pp. 850-853, vol. 122, No. 22. (Abstact Only).

Hedican, SP, "Complications of hand-assisted laparoscopic urologic surgery", J Endourol., May 2004, pp. 387-396, vol. 18, No. 4. (Abstract Only).

Batler, RA et al., "Hand-assisted laparoscopic radical nephrectomy: the experience of the inexperience", J Endourol., Jun. 2001, pp. 513-516, vol. 15, No. 5. (Abstract Only).

Siddins, Mark et al., Intraoperative vascular localization to facilitate endopyelotomy after renal transplantation, Australian and New Zealand Journal of Surgery, Aug. 2001, pp. 485, vol. 71, No. 8. (Abstract Only).

Binmoeller, KF et al., "Variceal bleeding and portal hypertension", Endoscopy, Mar. 2000, pp. 189-199, vol. 32, No. 3. (Abstract Only).

Riemann, JF et al., "Bleeding peptic ulcers—concept for acute therapy", Leber Magen Darm., Mar. 1995, pp. 71-74, vol. 25, No. 2. (Abstract Only).

"Sophisticated ultrasound Doppler and Emboli systems from DWL", [online] [retrieved on Sep. 8, 2003] Retrieved from internet <URL:http://www.cephalon.dk/dwl1.htm>, pp. 1-2. Cephalon A/S.

Snady, Harry, "Artifacts and Techniques of Endoscopic Ultrasonography in Investigating Gastrointestinal Pathologies and Theraputic Options", [online] [retrieved on Sep. 13, 2003] Retrieved from internet <URL:http://www.eusimaging.com/reference/papers/artifacts/artifacts_print.html>, pp. 1-18.

"Endoscopic Ultrasonography of the Layer Structure of the Gastric Walls", [online] [retrieved on Sep. 13, 2003] Retrieved from internet <URL:http://www.med.plig.org/10/42.html>, pp. 1-2.

Brucher, Rainer et al., "Automatice Online Embolus Detection and Artifact Rejection With The First Multifrequency Transcranial Doppler", Apr. 16, 2002, pp. 1969-1974, American Heart Assoc.

"Single-use VTI Intraoperative Reposable and Disposable Probes are quickly becoming indispensable tools in operating rooms around the world", pp. 1-4, Vascular Technology, MA.

"Ultasound System", [online] [retrieved on Sep. 13, 2003] Retrieved from internet <URL:http://www.olympus-russia.ru/index.php?section=endo>, pp. 1-5.

"EZ-Dop The Smallest Complete TCD Doppler System", pp. 1-2, DWL Systems, Inc., VA.

"Nicolet Elite Vascular applications", pp. 1-2, Nicolet Vascular.

"MedaSonics Model P82 (Pencil Style) Probe", pp. 1, CooperSurgical, Inc.

"Pencil-Type Immersion Transcucers", pp. 1, Piezo Technologies.

"Glossary-Vascular Surgery", Jul. 22, 2003, pp. 1-3, St. James's Hospital.

Liu, Julia et al., "Endoscopic Ultrasound Probes", Gastrointestinal Endoscopy, 2006, pp. 751-754, vol. 63, No. 6.

"Olympus Announces the Global Launch of the Universal Endoscopic Ultrasound Center EU-ME1", Feb. 16, 2009, [online] [retrieved on Apr. 6, 2009] Retrieved from the internet <URL:http://www.olympus-global.com/en/news/2009a/nr090216eume1e.cfm>.

* cited by examiner

System Block Diagram

System Block Diagram: FLOWMETER and Signal-Strength Meter

DOPPLER TRANSCEIVER AND PROBE FOR USE IN MINIMALLY INVASIVE PROCEDURES

RELATED APPLICATIONS

This application claims the benefit of U.S. Provisional Application No. 60/529,779, filed Dec. 16, 2003. This application is herein incorporated in its entirety by reference.

FIELD OF THE INVENTION

The invention relates to devices for use in minimally invasive procedures, and more particularly, to an endoscopic or laparoscopic device providing portable blood flow detection.

BACKGROUND OF THE INVENTION

There is often a need to identify blood vessels and assess blood flow status in identified vessels during minimally invasive medical procedures. In gastroenterologic endoscopy, examples of such instances include the identification of vessels in peptic ulcer bases, which guides subsequent management of these lesions, identification of vessels at risk prior to polypectomy, and identification of aberrant vessels at risk for bleeding prior to sphincterotomy. Other specialties would yield additional examples of such minimally invasive techniques and procedures.

Currently, vessels in peptic ulcer bases are only identified visually; these subjective observations are then used to grade ulcers via endoscopic stigmata of recent hemorrhage (ESRH) or similarly, the Forrest classification system. According to the Forrest Classification system, lesions are classified according to their appearance from a Class Ia to a Class III. The classes are as follows: Ia—spurting arterial hemorrhage, Ib—oozing hemorrhage, IIa—visible vessel, IIb—adherent clot, IIc—pigmented spot, III—no signs of recent hemorrhage. The use of ESRH or the Forrest classification system have been shown to be fraught with interobserver variability and the need for an objective method of grading peptic ulcer lesions to assess bleeding risk has been voiced by many in the GI field.

Furthermore, there is a need to assess the adequacy of endoscopic treatment of peptic ulcers. Currently, the GI endoscopist has no way of ascertaining whether an injection or coagulation therapy applied to an ulcer base has adequately occluded or obliterated the vessel at risk for recurrent bleeding. Despite advances in the endoscopic treatment of peptic ulcers, the rebleeding rate of lesions treated endoscopically remains high (quoted in the literature from less than 10% for combination therapies but as high as 30% for single therapies).

In addition, subsurface vessels are not readily visualized during laparoscopic procedures. Tactile sensation, which aids surgeons in the identification and evaluation of vessels in open surgical procedures, is not often available to the surgeon during laparoscopic surgery. In urologic surgery, the advancement of minimally invasive techniques has recently allowed for a laparoscopic approach to technically challenging procedures, which were previously only undertaken in an open fashion. Thus, there is an increasing need to identify blood vessels during laparoscopic urologic surgery Currently, subsurface vessels are identified by the use of anatomical landmarks and meticulous dissection techniques during laparoscopic urologic procedures. Meticulous dissection to identify a vessel, while necessary to avoid inadvertent injury to the vessel, adds significant time to the surgical procedure. In addition, vessels may be present in an "aberrant" anatomical pattern, making the use of landmarks deceiving. This is of increased significance during laparoscopic nephrectomy, during which several vessels have to be identified and control gained. Additionally, vessels can present aberrantly in 25-40% of kidneys. Finally, abundant fatty tissue surrounding the kidneys adds an additional layer of complication to the identification of the renal vasculature during laparoscopic nephrectomy.

Other indications in which the localization of the vasculature has become increasingly important include laparoscopic partial nephrectomy and laparoscopic nerve sparing radical prostatectomy. In partial nephrectomy, it is critical to identify the feeder artery to the tumor being excised while in radical prostatectomy, identification of the neurovascular bundle facilitates sparing of the cavernous nerves.

Other fields employing minimally invasive techniques such as arthroscopy, bronchoscopy, laryngoscopy, mediatinoscopy, thoracoscopy, cystoscopy, ureteroscopy, hysteroscopy, neuroendoscopy, robotic-assisted surgical procedures, and surgical fields in which laparoscopic surgery is utilized, present a similar inability to palpate tissue surfaces to assess blood flow. What is needed, therefore, are techniques and apparati for assessing blood flow during minimally invasive medical procedures.

BRIEF SUMMARY OF THE INVENTION

One embodiment of the present invention provides a system for the detection of blood flow, that system comprising: a transceiver unit comprising a signal generator having a plurality of preset signal sensitivity depth selectors, a signal comparator, and an audio output whereby a user receives an audio signal indicating differences in Doppler signal; an endoscopic Doppler probe coupled to the transceiver; that endoscopic Doppler probe comprising: a piezoelectric crystal disposed at a first end of the endoscopic Doppler probe; at least one wire transmitting signals between the transceiver unit to the piezoelectric crystal; a sheath disposed around at least part of at least one wire and piezoelectric crystal; and a transceiver unit coupler disposed at a second end of the endoscopic Doppler probe.

Another embodiment of the present invention provides such a system wherein the probe comprises a rigid sheath allowing for its insertion and use through a laparoscopic port.

Another embodiment of the present invention provides such a system wherein the transceiver is portable.

A further embodiment of the present invention provides such a system wherein the endoscopic probe is disposable.

A further embodiment of the present invention provides such a system wherein the laparoscopic probe is disposable.

Yet another embodiment of the present invention provides such a system further comprising at least one channel disposed within the sheath of the endoscopic probe.

A yet further embodiment of the present invention provides such a system wherein at least one channel of the endoscopic or laparoscopic probe is coupled to a tissue marking dye source, and whereby a tissue marking dye may be delivered to the first end of the endoscopic or laparoscopic Doppler probe.

Still another embodiment of the present invention provides such a system wherein at least one channel of the endoscopic or laparoscopic Doppler probe is coupled to a vacuum source, and whereby a vacuum may be applied to a target, steadying the endoscopic or laparoscopic Doppler probe proximate to the target.

Yet another embodiment of the present invention, provides such a system wherein both a tissue marking device and a probe stabilization device are coupled to the endoscopic or laparoscopic Doppler probe.

Another embodiment of the present invention provides such a system wherein the Doppler probe is combined with endoscopic or laparoscopic instruments, providing for "Doppler enabled" instrumentation for endoscopic or laparoscopic use.

A still further embodiment of the present invention provides such a system further comprising a quantitative blood flow meter.

Even another embodiment of the present invention provides such a system wherein the blood flow meter comprises a numeric display.

Still another embodiment of the present invention provides such a system further comprising a quantitative measure of the strength of the Doppler signal, herein referred to as a signal strength meter.

A still further embodiment of the present invention provides such a system wherein the signal strength meter comprises a numeric display.

An even further embodiment of the present invention provides a method for the assessment of blood flow, that method comprising: inserting a Doppler probe into an endoscope; positioning a pulsed Doppler probe proximate to a target region; selecting a depth of signal sensitivity from a plurality of preset signal depths; emitting at least one pulse from the Doppler probe; receiving at least one reflected pulse; generating an audio signal correlating to the velocity of blood flow; and assessing blood flow based on the audible signal.

Another embodiment of the present invention provides such a method further comprising providing a quantitative measure correlating to velocity of the blood flow.

Another embodiment of the present invention provides such a method further comprising providing a quantitative measure correlating to the strength of the Doppler signal produced by the blood flow.

A further embodiment of the present invention provides such a method wherein the assessment of blood flow is employed in at least one medical procedure, selected from the group of medical procedures consisting of assessment of esophageal varices, esophageal ulcers, Mallory-Weiss tears, gastric varices, Dieulafoy's lesion, AVMs, vascular malformations, post-haemostatic treatment assessment, and pre-operative assessment of incision sights for sphincterotomy, polypectomy and cyst drainage.

An even further embodiment of the present invention provides a method for the assessment of blood flow, that method comprising: inserting a Doppler probe into a laparoscopic port; positioning a pulsed Doppler probe proximate to a target region; emitting at least one pulse from the Doppler probe; receiving at least one reflected pulse; generating an audio signal correlating to the velocity of blood flow; and assessing blood flow based on the audible signal.

Another embodiment of the present invention provides such a method further comprising providing a quantitative measure correlating to velocity of the blood flow.

Another embodiment of the present invention provides such a method further comprising providing a quantitative measure correlating to the strength of the Doppler signal.

A further embodiment of the present invention provides such a method wherein the assessment of blood flow is employed in at least one laparoscopic urologic procedure, selected from the group of laparoscopic urologic procedures consisting of radical nephrectomy, donor nephrectomy, partial nephrectomy, radical prostatectomy with nerve sparing, retroperitoneal pelvic lymph node dissection, pelvic lymph node dissection, pyeloplasty, varicocelectomy and adrenalectomy.

An additional embodiment of the present invention provides a system for the quantitative assessment of blood flow, that system comprising: a transceiver unit comprising a signal generator, a signal comparator, and an audio output whereby a user receives an audio signal indicating differences in Doppler signal; a Doppler probe coupled to the portable transceiver; the Doppler probe comprising: a piezoelectric crystal disposed at a first end of the Doppler probe; at least one wire transmitting signals between the transceiver unit to the piezoelectric crystal; a rigid or flexible sheath disposed around at least part of the at least one wire and the piezoelectric crystal; a transceiver unit coupler disposed at a second end of the Doppler probe; and a flow meter comprising a visual quantitative display and a zero-crossing detector.

Another embodiment of the present invention provides such a system further comprising a signal strength meter providing a visual quantitative measure of the strength of the Doppler signal.

Another additional embodiment of the present invention provides such a system further comprising a plurality of preset signal sensitivity depth selectors.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
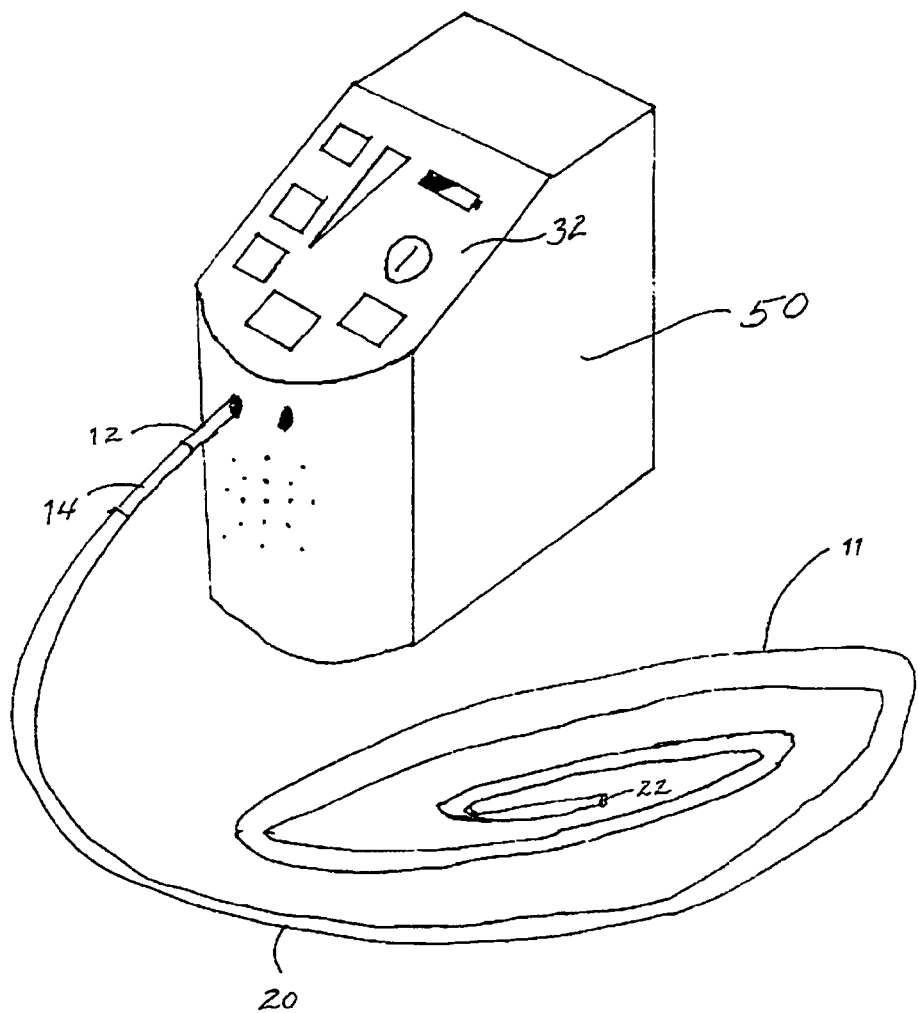
FIG. 1 is a perspective view illustrating an endoscopic Doppler transceiver and probe configured in accordance with one embodiment of the present invention.

One embodiment of the present invention provides a non-imaging Doppler system (i.e. one without an ultrasonic images of tissues, but not excluding other visual cues or displays) for use in minimally invasive surgical or medical techniques, such as endoscopy or laparoscopy providing a portable audio blood flow detector, which allows for the identification and assessment of critical blood vessels. One embodiment of the present invention, illustrated in FIG. 1 provides a disposable Doppler probe 11, which can be inserted through the working channel of an endoscope, a laparoscopic port, or other such suitable entry point, and a portable transceiver unit 50, which transmits the Doppler signal in an auditory fashion. A varying audible signal is produced when the crystal 22 of probe 11 is placed upon a vessel within which there is blood flow. The frequency (i.e., pitch) of the signal is proportional to the blood velocity within the vessel. Distinctive tonal patterns are produced which are indicative of the flow pattern in terms of velocity vs. time.

One skilled in the art will readily appreciate that an endoscopic Doppler probe 11 configured according to one embodiment of the present invention would be susceptible to a variety of uses. For instance, an endoscopic Doppler probe 11 could be used to interrogate peptic ulcers, not only to assess the adequacy of endoscopic therapy, but also to guide the initial management of these lesions from a diagnostic point of view.

In addition to its utility in peptic ulcer disease, an endoscopic Doppler probe 11 could be used to decrease bleeding complications associated with sphincterotomy. One to two percent of sphincterotomies are complicated by significant hemorrhage, often secondary to an aberrant branch of the retroduodenal artery. Although this risk of significant hemorrhage seems relatively low, it is often described as a "clinical disaster" when it occurs and has little recourse. Probing the sphincter prior to incision would allow the physician to identify vessels at risk for bleeding; this would allow for a more optimal selection of the incision site. In addition to the above-mentioned indications, an endoscopic Doppler probe could have utility in the treatment of esophageal varices, colonic and other polyps and other GI lesions. One skilled in the art will readily appreciate that many other applications for a minimally invasive Doppler system during endoscopic procedures exist.

One method of using the endoscopic Doppler probe of one embodiment of the present invention involves, introducing an endoscope into a body cavity of a patient, visually identifying a target to probe, introducing a probe 11 through the endoscopic channel, directing the probe to the region to be investigated by manipulating the endoscope and the probe 11 to achieve contact of the Doppler probe 11 with the desired tissue target region, transmitting ultrasonic waves, receiving reflected ultrasonic waves (echoes), determining the Doppler shift of the echoes, generating an audio signal which correlates to the velocity of blood flow, and thus providing the endoscopist with a means to detect and assess blood flow within the gastrointestinal tract. The endoscopist can alter the incident angle of contact between the probe 11 and the tissue by manipulating the tip of the endoscope and the probe 11 and the endoscope to optimize the Doppler signal.

Figure 3:
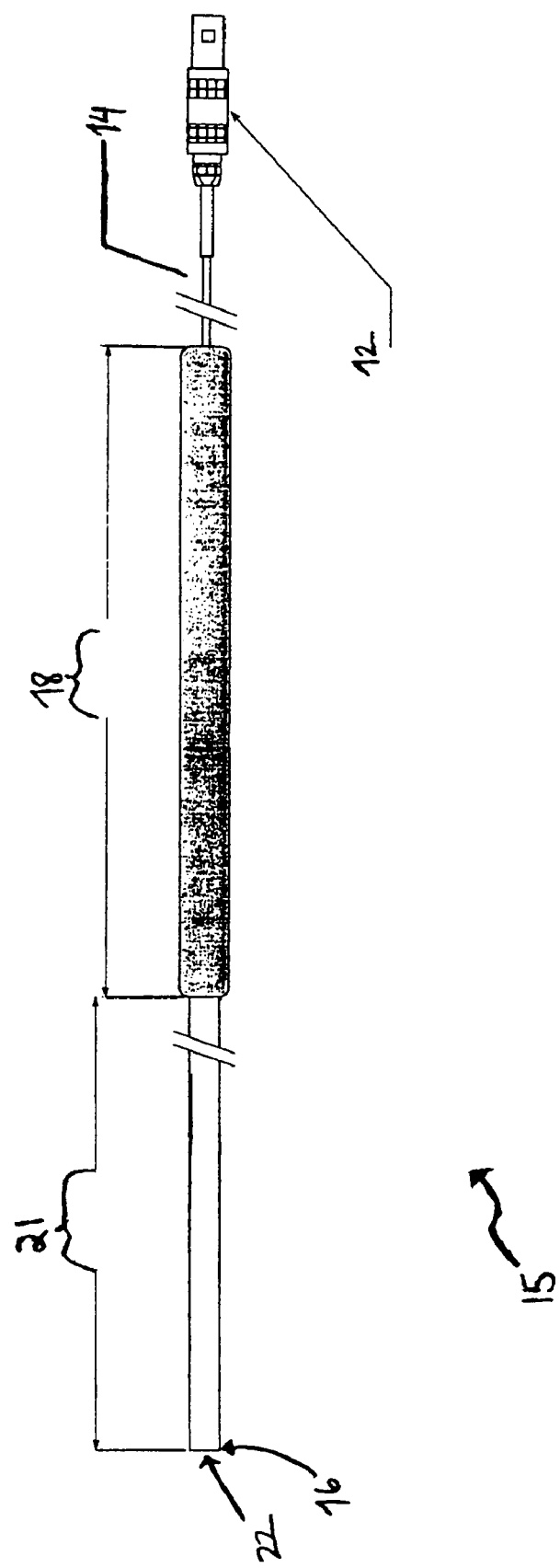
FIG. 3 is an elevation view illustrating a laparoscopic Doppler probe configured in accordance with one embodiment of the present invention.

One skilled in the art will also readily appreciate that a laparoscopic Doppler probe 15, configured according to one embodiment of the present invention illustrated in FIG. 3 would be susceptible to a variety of uses. For instance, such a laparoscopic Doppler probe 15 could be used to localize vessels during laparoscopic radical or donor nephrectomy, not only to facilitate their identification but also to assess that adequate haemostatic control of these vessels has been achieved.

In addition to its utility in laparoscopic nephrectomy, a laparoscopic Doppler probe 15 could be used to identify feeder arteries during partial nephrectomy. Furthermore, a laparoscopic Doppler probe 15 could have utility in radical prostatectomy with nerve sparing, retroperitoneal pelvic lymph node dissection, pelvic lymph node dissection, pyeloplasty, varicocelectomy and adrenalectomy. One skilled in the art will readily appreciate that many other applications for a minimally invasive Doppler system during laparoscopic procedures exist in other surgical and medical procedures and specialties.

A method of using the laparoscopic Doppler probe 15 of one embodiment of the present invention involves, introducing a laparoscopic port at a surgically optimal location within the patient, visually identifying a target to probe, introducing a probe 15 through the laparoscopic channel, directing the probe to the region to be investigated by manipulating the probe 15 to achieve contact of the Doppler probe 15 with the desired tissue target region, transmitting ultrasonic waves, receiving reflected ultrasonic waves (echoes), determining the Doppler shift of the echoes, generating an audio signal which correlates to the velocity of blood flow, and thus providing the surgeon with a means to detect and assess blood flow during the laparoscopic procedure. The surgeon can alter the incident angle of contact between the probe 15 and the tissue by manipulating the probe 15 to optimize the Doppler signal.

Figure 2:
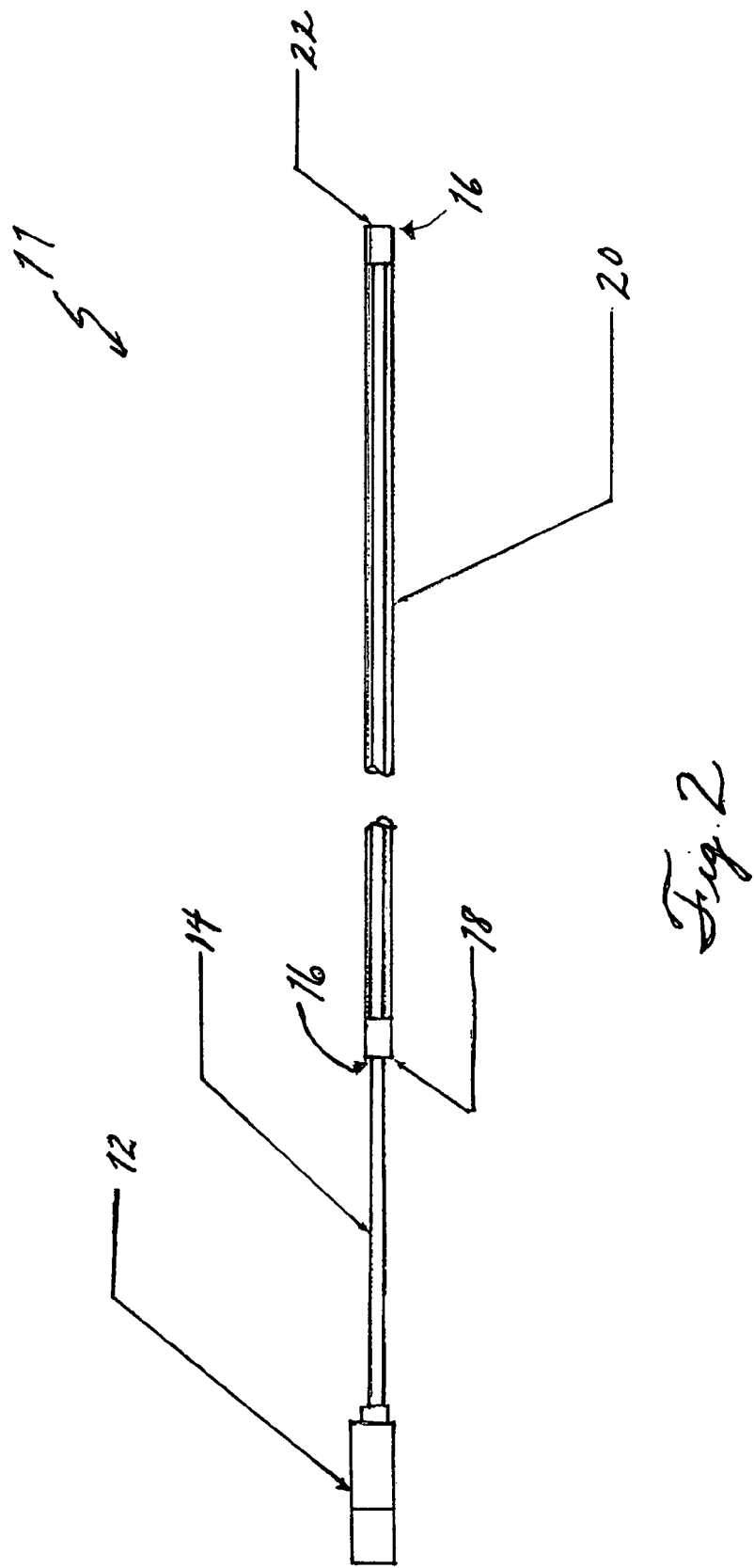
FIG. 2 is an elevation view illustrating an endoscopic Doppler probe configured in accordance with one embodiment of the present invention.

One embodiment of the invention, illustrated in FIGS. 2 and 3, provides a disposable endoscopic or laparoscopic Doppler probe 11, 15. Single-use probes optimize patient safety by decreasing the likelihood of cross contamination between patients. Single use probes 11, 15 are not susceptible to the degradation in reliability occasioned by repeated sterilization of the Doppler crystal. According to one embodiment, the probe consists of a piezoelectric crystal 22 at its tip, which transmits and then receives ultrasound signals into and from the tissue. Wires 14 attached to the crystal run the length of the probe and terminate at a coaxial connector 12, which provides the attachment of the probe 11 or 15 to the Doppler transceiver 50. In one embodiment, the endoscopic probe, the piezoelectric crystal 22 and at least 165 cm of the distal wiring is sheathed in a flexible yet resilient material 20, which allows for easy insertion of the probe through the endoscopic channel. In an alternative embodiment, wiring with a desired stiffness could be employed in lieu of housing the wire within a sheath. The sheath 20 may be bonded at ends 18 with biocompatible epoxy 16. The diameter of the sheath 20 will vary depending on the intended use of the probe and the endoscope channel with which it is used. For example, for use with a standard upper GI endoscope, the tubing outer diameter of the sheath should not exceed about approximately 2.8 mm. Other embodiments, for instance, such as that used in colonoscopic applications, the outer diameter of the sheath may be up to approximately 3.2 mm. The sheath 20 must fit in through the endoscopic channel, and be appropriately sized to allow the probe 11 to be freely articulated by the user. Similarly, the length of both the wire 14 and of the sheath 20 varies according to the application. In one embodiment, the length of the wire 14 is 240 cm with a 165 cm sheath. An alternative embodiment provides a probe 11 having a sheathed probe 20 length of about approximately 230 cm or greater for insertion of the probe through a colonoscope. This embodiment has total length of the Doppler probe of at least 305 cm. One of ordinary skill in the art will readily appreciate that other embodiments having a variety of diameters and lengths are within the scope of the present invention.

In one laparoscopic embodiment of the probe 15, the piezoelectric crystal 22 and about approximately 25 cm of the distal wiring is sheathed in a rigid tubing material 21, which allows for easy insertion of the probe through the laparoscopic port. Alternative to sheathing, wiring with a desired stiffness could be employed. The diameter of the cylinder 21 will vary depending on the intended use of the probe and the laparoscopic port with which it is used. For example, for use with a standard 5 mm port, the outer diameter of the cylinder 21 should not exceed 5 mm. Other embodiments, for instance, such as that used in minilaparoscopic applications, the outer diameter of the cylinder 21 may be up to approximately 2.0 mm. The cylinder 21 must fit in through the laparoscopic port, and be appropriately sized to allow the probe 15 to be freely articulated by the user. Similarly, the length of both the wire 14 and of the rigid tube 21 varies according to the application. In one embodiment, the length of the wire 14 is 240 cm with 25 cm rigid tubing. Again, one of ordinary skill in the art will readily appreciate that other embodiments having a variety of diameters and lengths are within the scope of the present invention.

Sheathing 20 for the endoscopic probe is achieved, according to one embodiment, with plastic tubing produced from a plastic having the desired flexibility, biocompatibility, and other desired physical properties, which optimizes both cost effectiveness and functionality during endoscopy. One example of such a plastic is polytetrafluoroethylene (PTFE). Alternative sheathing 20 can be achieved with coil spring (utilizing 2 coils wound side by side), braid tubing, or other materials. For a laparoscopic probe, sheathing 21 may be achieved with a tube produced from a material having the desired rigidity, biocompatibility, and other desired physical properties, which optimizes both cost effectiveness and functionality during laparoscopic surgery. One example of such a material is stainless steel. Alternative sheathing 21 can be achieved with rigid plastic tubing such as HDPE. The piezoelectric crystal 22 and wiring 14 assembly is optimally bonded to the sheathing material using a biocompatible epoxy in both probes. These assemblies are illustrated in FIGS. 2 and 3.

Figure 4:
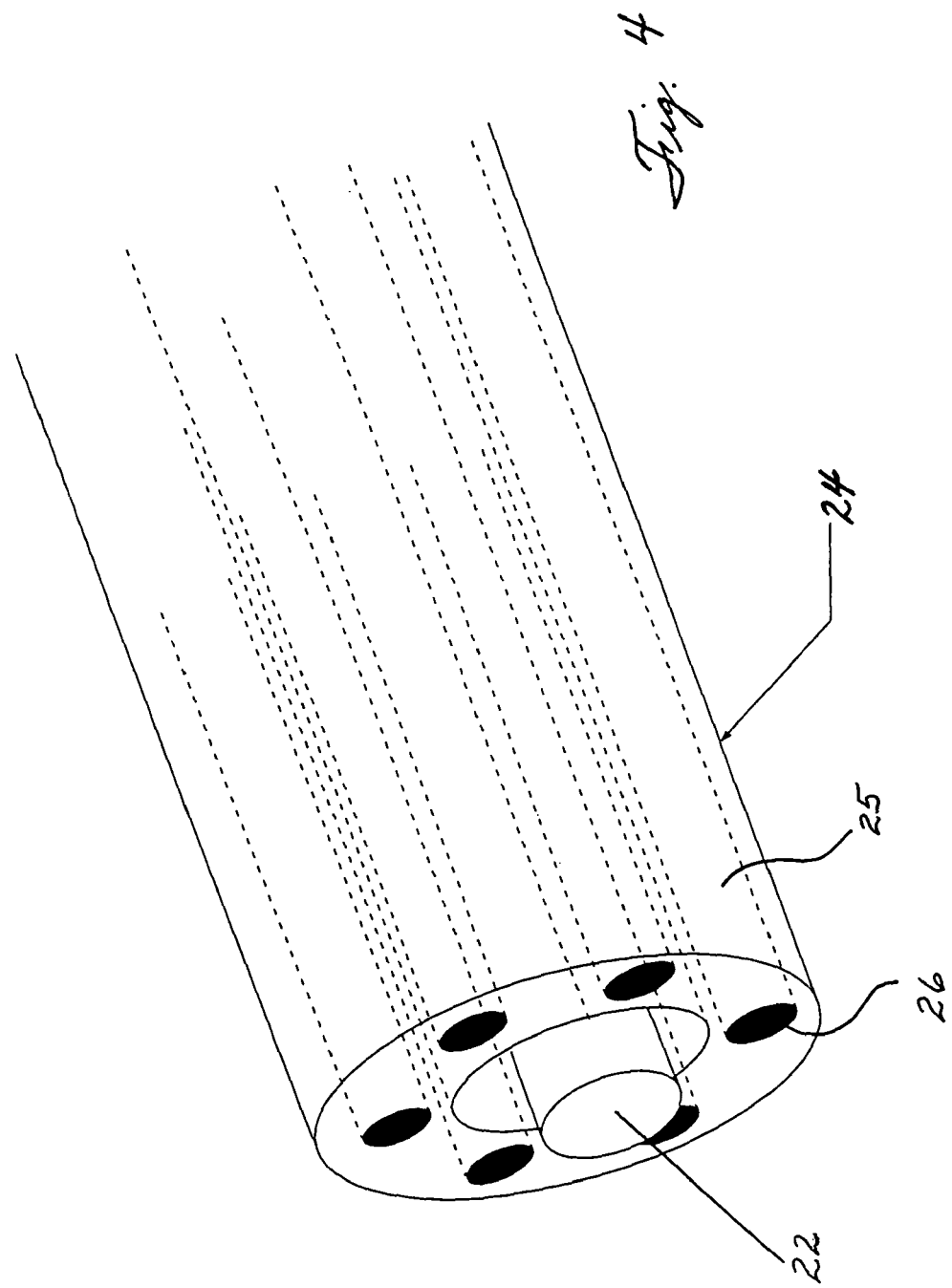
FIG. 4 is a perspective view illustrating an endoscopic Doppler probe having a tissue-marking device configured in accordance with one embodiment of the present invention.

According to one embodiment of the present invention, illustrated in FIG. 4, a mechanism is incorporated into the probe that allows for marking of tissue at desired locations. In this variation, wires/tubes or a series of wires/tubes 25 are embedded in or placed adjacent to the wall 24 of the sheathing material with distal openings 26 at the probe tip 22, and running parallel to the sheath. Another means by which this can be achieved is by employing an extrusion process to create a multilumen tubular sheath. The wires or tubes 25 are connected to a delivery system that physically passes or electrically promotes the application of a tissue marking dye to the tissue directly adjacent to the tip of the piezoelectric crystal 22. The delivery system may consist of but is not limited to an injection system or a surface marking system. This marking system allows the user to readily identify the point at which a Doppler signal is elicited, even after the Doppler probe 11 is withdrawn. The total diameter of the Doppler probe 11 with additional tubing/wiring would be of a diameter to allow facile articulation of the probe.

Figure 5:
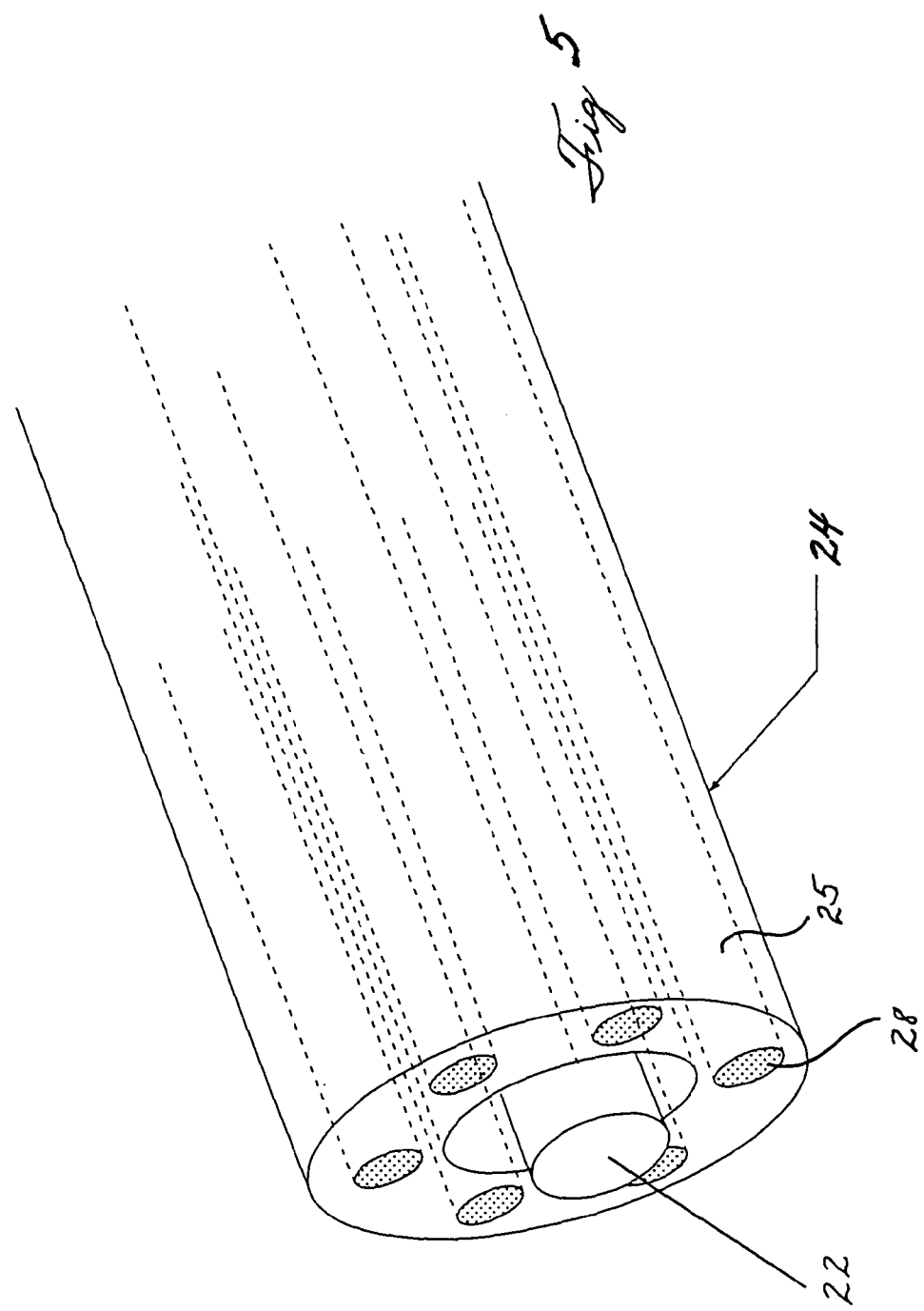
FIG. 5 is a perspective view illustrating an endoscopic Doppler probe having a probe-stabilizing device configured in accordance with one embodiment of the present invention.

One embodiment of the present invention, illustrated in FIG. 5, also provides a probe-stabilizing device. During GI endoscopy and other similar procedures, the inherent motion of the digestive tract and external motions, such as patient movement, make it difficult to maintain a probe in position at a discrete location for an extended period of time. Thus, a mechanism allowing the user to maintain the probe in a particular position would be clinically useful. One such device consists of a gentle suction device 28 located adjacent to and running parallel with the probe sheath. This device 28 would consist of a tubing 25 material with its distal opening flush with the probe tip 22 and proximal opening connected to a gentle vacuum system. Application of the vacuum would cause the distal probe tip 22 to adhere to the adjacent tissue, allowing the user to maintain the probe's 11 position until the vacuum was shut off, or until movements of the tissue/endoscope exceeded the vacuum force. The vacuum force applied would be controlled by an external regulator and would not exceed a force that would cause damage to the surrounding tissue. The total diameter of the Doppler probe 11 with additional vacuum tubing would not exceed the diameter of the opening of the endoscopic channel. In another embodiment, electrically activated adhesive pads would be placed adjacent to the probe tip 22 with wiring running parallel to the probe sheath. The application of a low voltage current would result in the adherence of the adhesive pads to the adjacent tissue; deactivation of the current would allow the probe tip 22 to be removed from the tissue. The electrical current applied would be below the level at which damage would be induced to the surrounding tissue.

Figure 6:
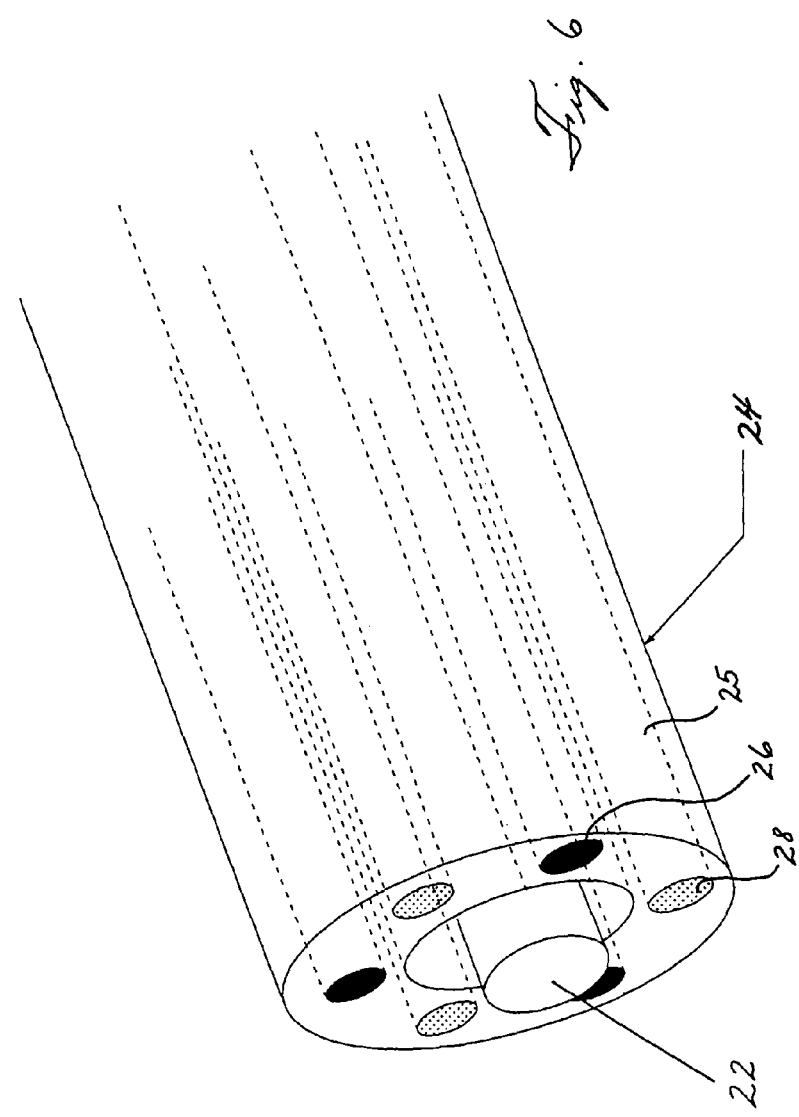
FIG. 6 is a perspective view illustrating an endoscopic Doppler probe having a probe stabilization device and a tissue-marking device configured in accordance with one embodiment of the present invention.

One embodiment of the present invention, illustrated in FIG. 6, provides both a tissue marking device and a probe stabilization device. In this embodiment, tubing/wiring 25 adjacent to or embedded within the sheathing material 20 could be used either for the application of a vacuum force or for the electrical activation of adhesion pads, and also for the delivery or application of a tissue marking dye as described in the paragraphs above.

Figure 7:
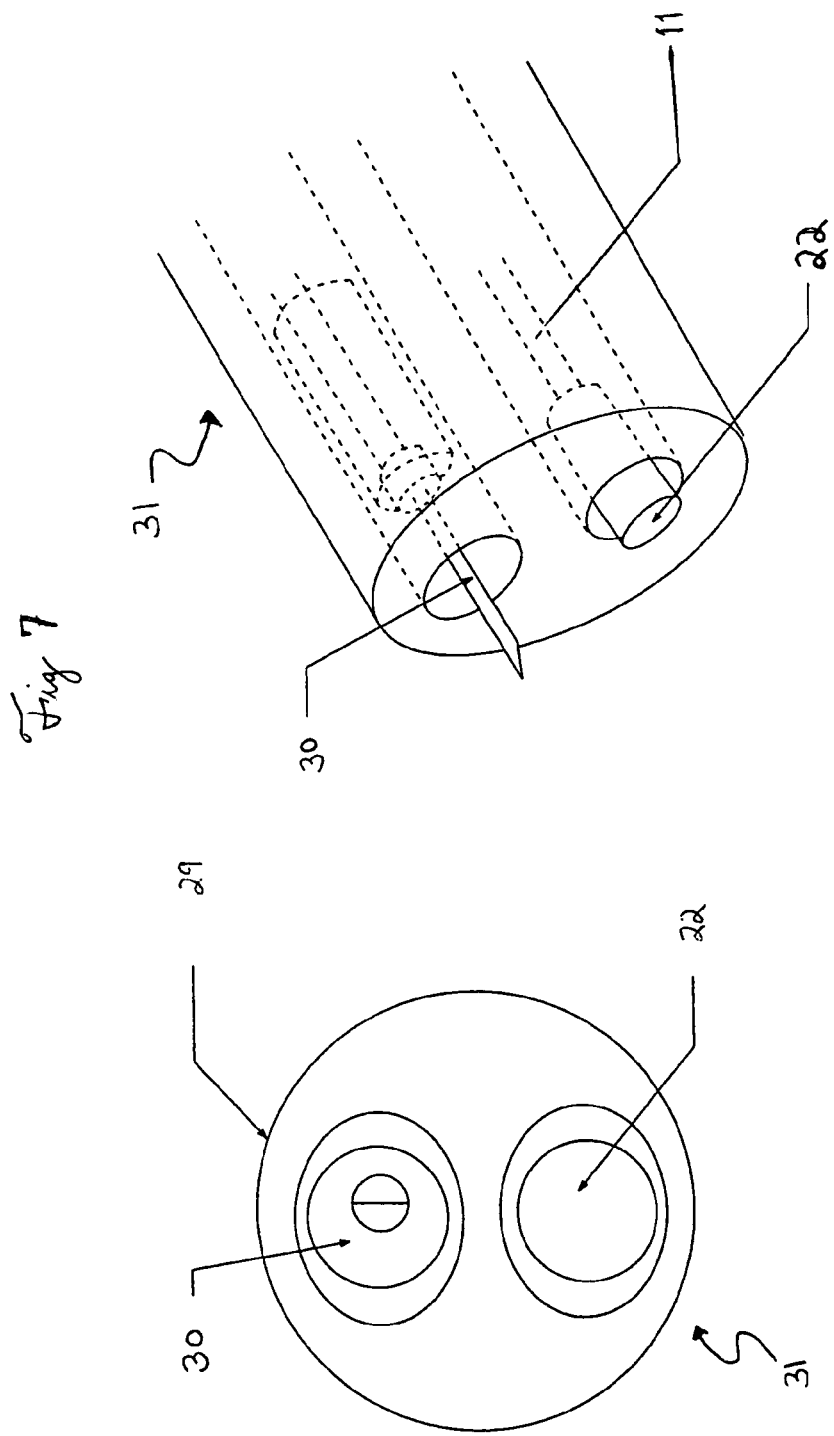
FIG. 7 is a perspective view illustrating an endoscopic Doppler probe combined with an endoscopic instrument in accordance with one embodiment of the present invention.

One embodiment of the present invention, illustrated in FIG. 7, provides a Doppler probe 11 combined with an endoscopic instrument such as an endoscopic injection needle 30. This embodiment provides for "Doppler enabled instrumentation" and can be applied to endoscopic as well as laparoscopic tools. According to one such embodiment, the sheathing for the Doppler probe 11 is combined with the tubular body of the endoscopic instrument 31. One means by which this can be achieved is by employing an extrusion process to create a double lumen tubular sheath 29. One lumen of the tubing houses the endoscopic instrumentation, such as an endoscopic injection needle 30, while the second lumen houses the Doppler probe 11. The double lumen tubular sheath 29 could employ a flexible yet resilient material such as polytetrafluoroethylene (PTFE). Other plastic materials could also be used. Similarly, a Doppler probe could be combined with a laparoscopic instrument. In this embodiment, extruded high density polyethylene (HDPE) tubing could provide a double lumen sheath 29 with the rigidity needed for laparoscopic procedures. Alternatively, two stainless steel tubes could be welded together to form the housing for the Doppler and laparoscopic instrument.

Figure 8:
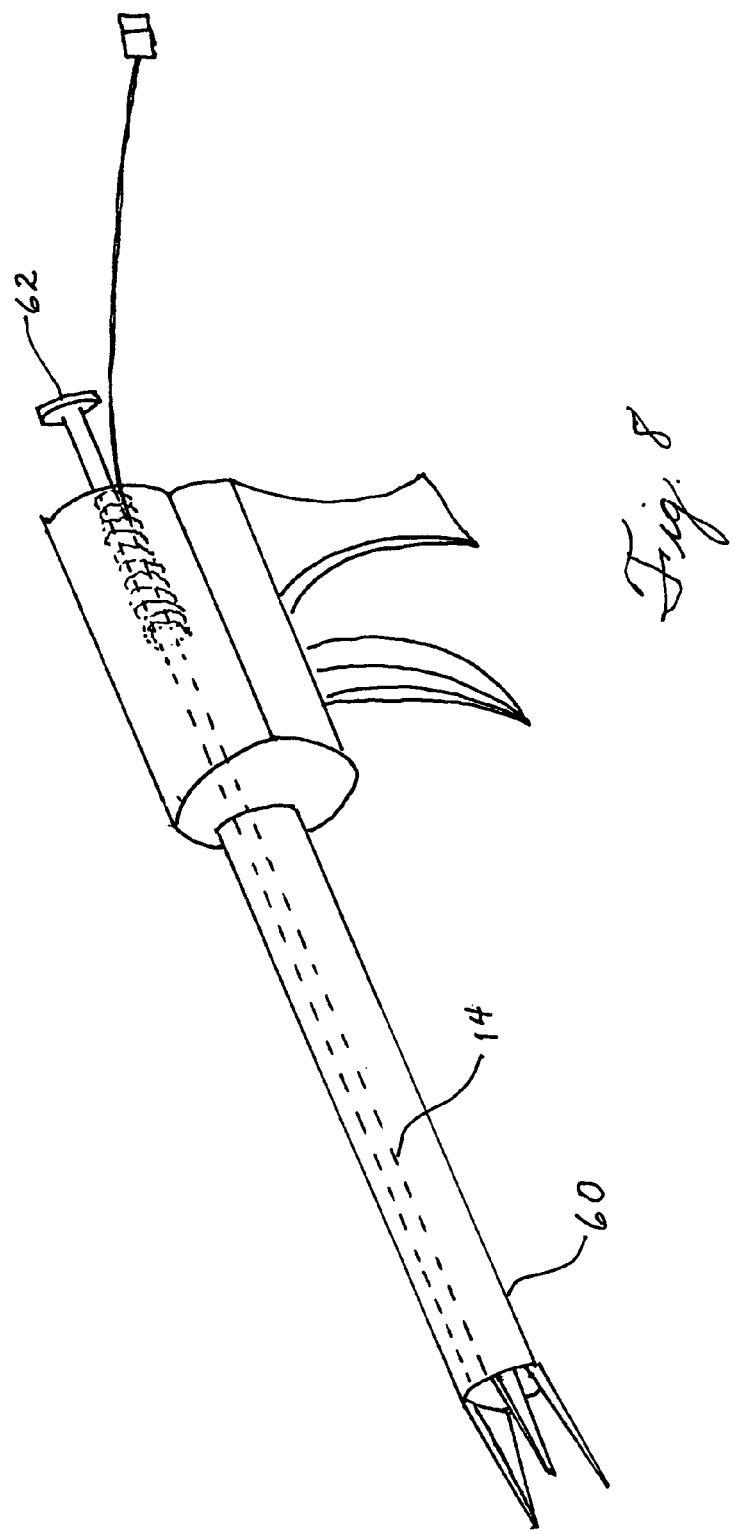
FIG. 8 is a perspective view illustrating a laparoscopic Doppler probe combined with a laparoscopic instrument in accordance with one embodiment of the present invention.

Another means by which "Doppler enabled instrumentation" could be achieved would be to position the Doppler probe (consisting of the piezoelectric crystal and wire) within the body of the instrument, as illustrated in FIG. 8. In such an embodiment, the piezoelectric crystal 22 would be placed within the tubular portion 60 of the instrument or attached to the instrument itself. The Doppler wire 14 would course through or adjacent to the tubular portion of the instrument and end in a coupler that could be attached to a Doppler transceiver. The Doppler assembly could be fixed in position or could be made retractable using a mechanical plunger mechanism 62 or similar appropriate technique. A laparoscopic clip applier as illustrated in FIG. 8 would be one example of this embodiment.

The combination of the Doppler probe 11,15 with a therapeutic endoscopic or laparoscopic instrument such as an injection needle or clip applier allows the physician to identify a vessel and treat it without the need to remove and reinsert instrumentation. This not only saves time but also allows for more precise treatment of the vasculature. Instruments that could be combined with a Doppler probe include but are not limited to injection needles, heater probes, monopolar or bipolar coagulation probes, haemostatic clips, band ligators, dissectors, scissors, and forceps.

Figure 9:
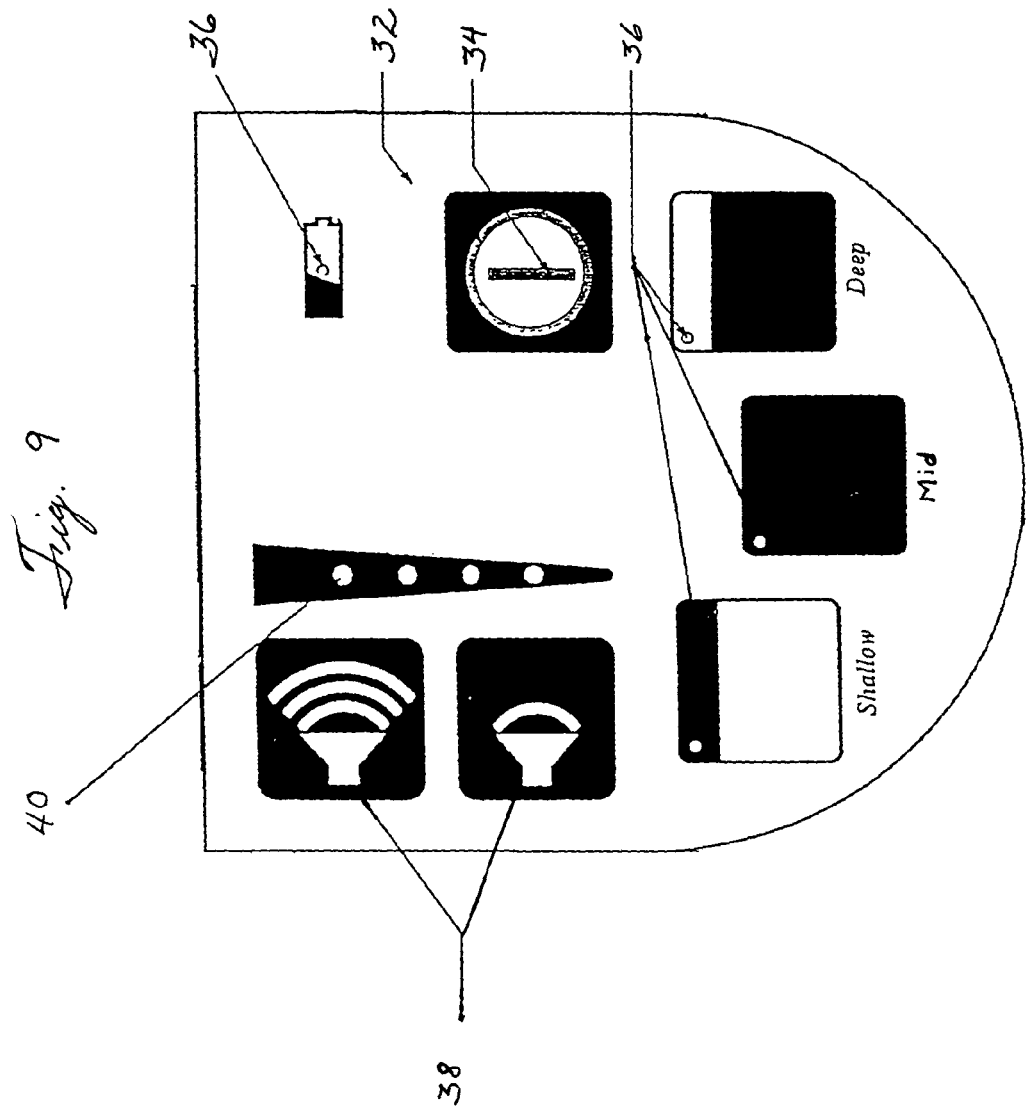
FIG. 9 is a plan view illustrating a control panel for an endoscopic Doppler transceiver configured in accordance with one embodiment of the present invention.
Figure 10:
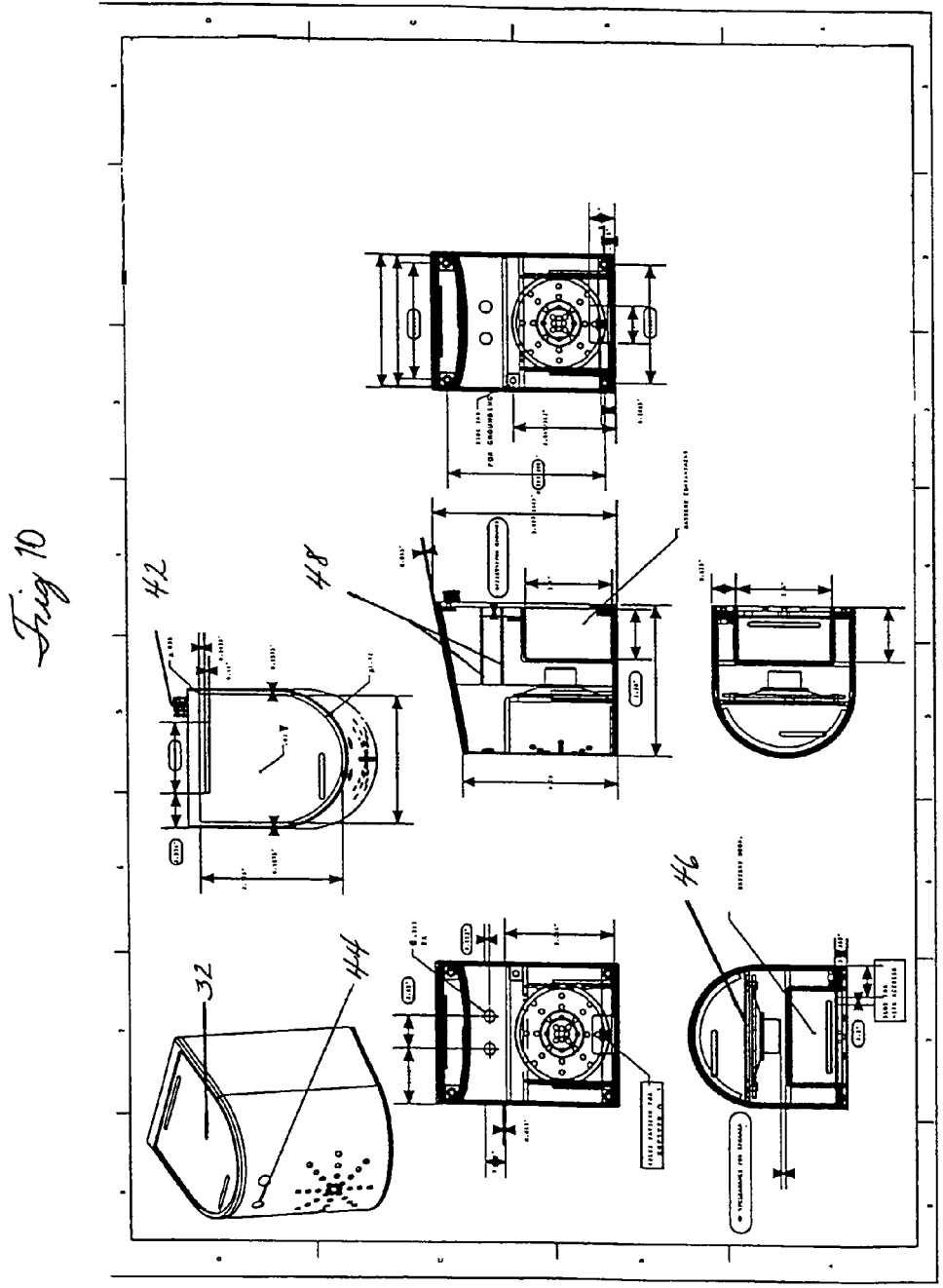
FIG. 10 is a collection of views illustrating an endoscopic Doppler transceiver configured in accordance with one embodiment of the present invention.

One embodiment of the present invention, illustrated in FIGS. 1, 10, 11, and 14, provides a portable ultrasound transmitting and receiving device 50, which determines the Doppler shift of a flowing medium and converts this information into an audible signal emitted by a speaker 46. According to such an embodiment, an 8 or 20 MHz ultrasound transmission frequency is employed; however, other frequency signals can be used. Circuit boards 48 are disposed within the transceiver. The probe connects to the transceiver at a connection port 44. The transceiver has a control panel 32 of one embodiment, illustrated in FIG. 9, which in one embodiment incorporates a power button 34, at least one volume control button 38, a low battery indicator light 35 and at least one button for depth selection 36. A volume indicator 40 may also be provided. The depth selection buttons 36 are, according to one embodiment, a set of three buttons: Shallow, Deep and Mid, and in one embodiment are set at 0-1.5 mm, 0-7 mm and 0-4 mm respectively. In another embodiment of the unit, these settings can be modified to represent different depths of Doppler signal sensitivity. Variable depths of Doppler signal sensitivity are achieved by varying the length of the transmit pulse, and enabling variable time gates which define the periods during which the transducer transmits and receives signals. These variables are determined by logic circuits embedded in an electrically programmable CPLD (complex programmable logic device). In one embodiment, the device has 72 programmable logic blocks consisting of a single flip-flip and a programmable logic gate matrix. The programmed CPLD implements an 8 bit counter and a state decode which produces the 20 MHz transmit burst and the desired gate enable. Two control flip-flops which define the "mode/state" the device is in are also programmed onto this device. In one embodiment, there are three allowed states—"shallow", "mid" and "deep". The physician may select a specific state by pressing one of the three depth selection buttons on the control panel or may cycle the flip-flops through the states using a single footswitch. The depth selection feature allows the user to interrogate the tissue for blood flow at predetermined depths from the surface. One skilled in the art will readily appreciate that while the specific depths chosen here are clinically relevant to the realm of GI endoscopy, they do not preclude the relevance of other depths or their incorporation into the VTI Endoscopic Doppler System.

According to one embodiment, the Doppler transceiver 50 also incorporates a connector 42 for a remote control device which could include a foot pedal, a hand held remote system or other similar device for remote operation of the transceiver unit. A speaker 46 is, according to one embodiment, incorporated into the transceiver 50 for transmission of the auditory signal. Overall, the transceiver 50 is compact and designed for portable use. According to one embodiment it measures 3.75×5.25×4.25 inches and weighs less than 1.5 lbs. Its battery-powered operation further facilitates its portability.

Figure 11:
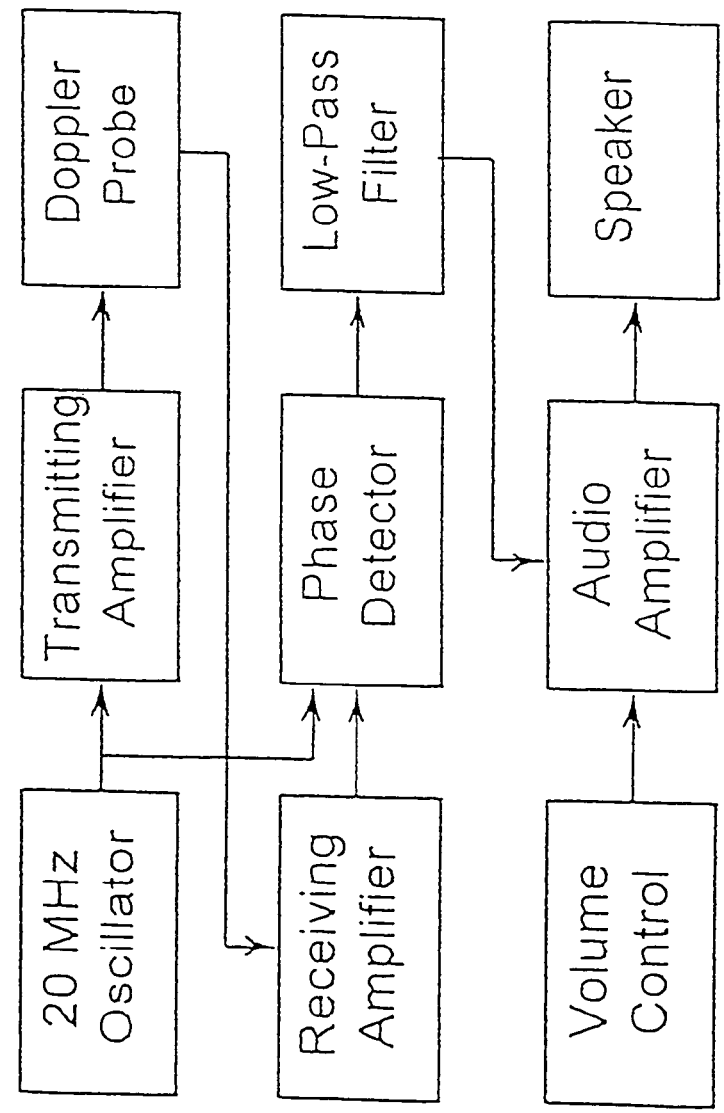
FIG. 11 is a block diagram illustrating a Doppler transceiver and probe system configured in accordance with one embodiment of the present invention.

FIG. 11 is a block diagram illustrating the function of the Doppler transceiver 50 as it generates, transmits and receives back the ultrasonic signal, determines the Doppler shift and generates an audible output representing this shift. According to one embodiment of the present invention, eight standard AA (LR6) alkaline batteries power the transceiver 50. One skilled in the art will readily appreciate that such batteries are just one possible power source and that various embodiments may be configured that operate on alternating current, or direct current sources may be provided that are rechargeable or provide other benefits, and that all such embodiments are within the scope of the present invention. In one embodiment, an 8 or 20 MHz oscillator in the transceiver 50 periodically drives the ultrasonic transmitting crystal 22 located at the tip of the probe 11 or 15. The ultrasonic waves generated by the crystal 22 travel through the tissue just under the probe 11 or 15 tip in a fairly narrow beam. Waves encountering moving objects are reflected back towards the probe 11 or 15 with a frequency shift proportional to the velocity of the moving object. During the intervals when the unit is not transmitting, the crystal 22 of probe 11 or 15 receives and passes reflected signals to a receiving circuit. This circuit amplifies the returning echoes and then multiplies these received signals with the oscillator frequency (at the phase detector) to shift the returned signals into an audible range. A band pass filter then acts to reject those frequencies received at exactly 8 or 20 MHz respectively, and also those frequencies received exactly at the pulse repetition frequency. The frequencies that remain are amplified via an audio amplifier and are transmitted through the speaker of the transmitter; volume control keys on the membrane control switch can be used to adjust the volume of the transmitted Doppler signal. In another embodiment, the Doppler signal can also be displayed graphically via use of an LCD screen or graphing printer connected to the Doppler transceiver or other such graphic output means well know to those skilled in the art. Varying depths of signal sensitivity are achieved by varying the length of the transmit pulse and enabling time gates.

Figure 13:
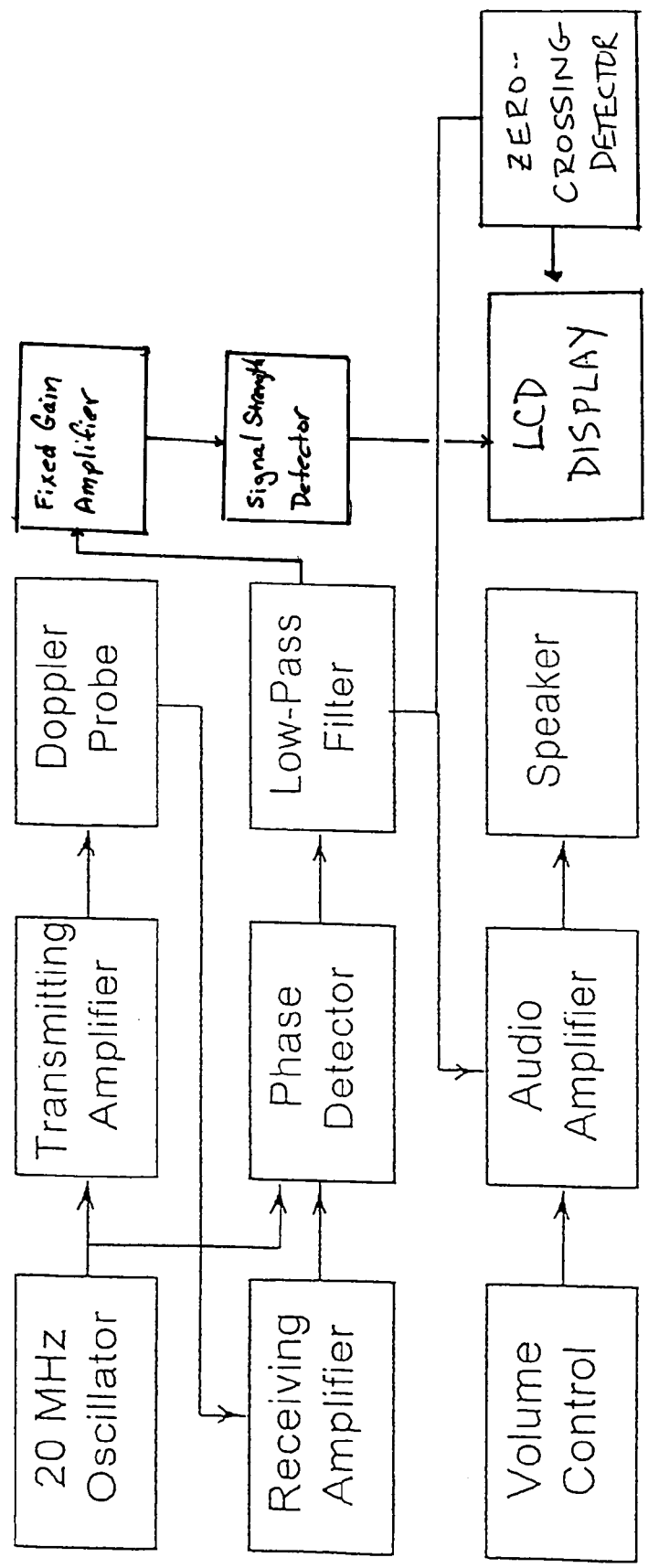
FIG. 13 is a block diagram illustrating a Doppler transceiver and probe system having a flow meter and signal strength meter configured in accordance with one embodiment of the present invention.
Figure 14:
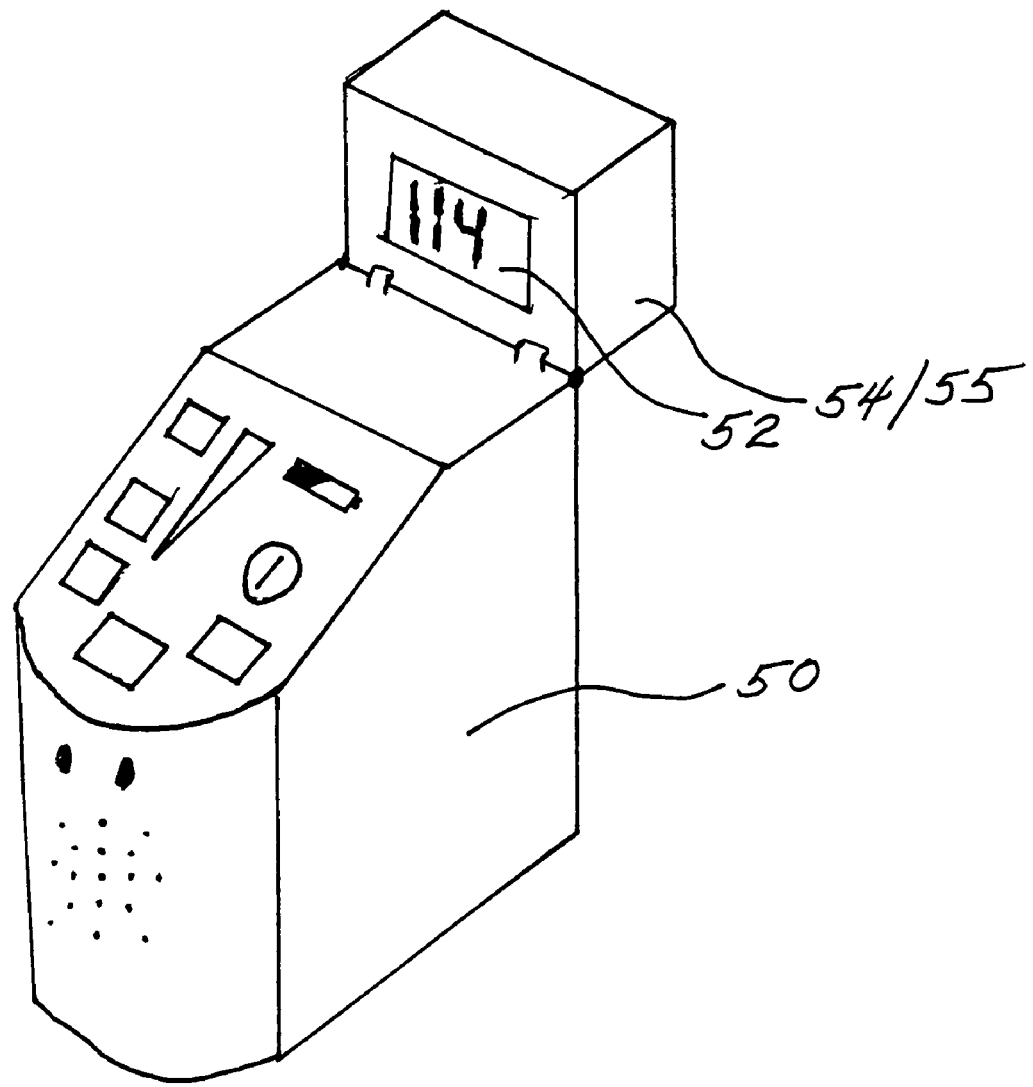
FIG. 14 is a perspective view illustrating a Doppler transceiver and probe system having a flow meter and a signal strength meter configured in accordance with one embodiment of the present invention.

Another embodiment of the present invention, illustrated in FIGS. 13 and 14 provides a Doppler probe and transceiver 50 having a "flow meter" and/or "signal strength meter" function and display 52.

Figure 12:
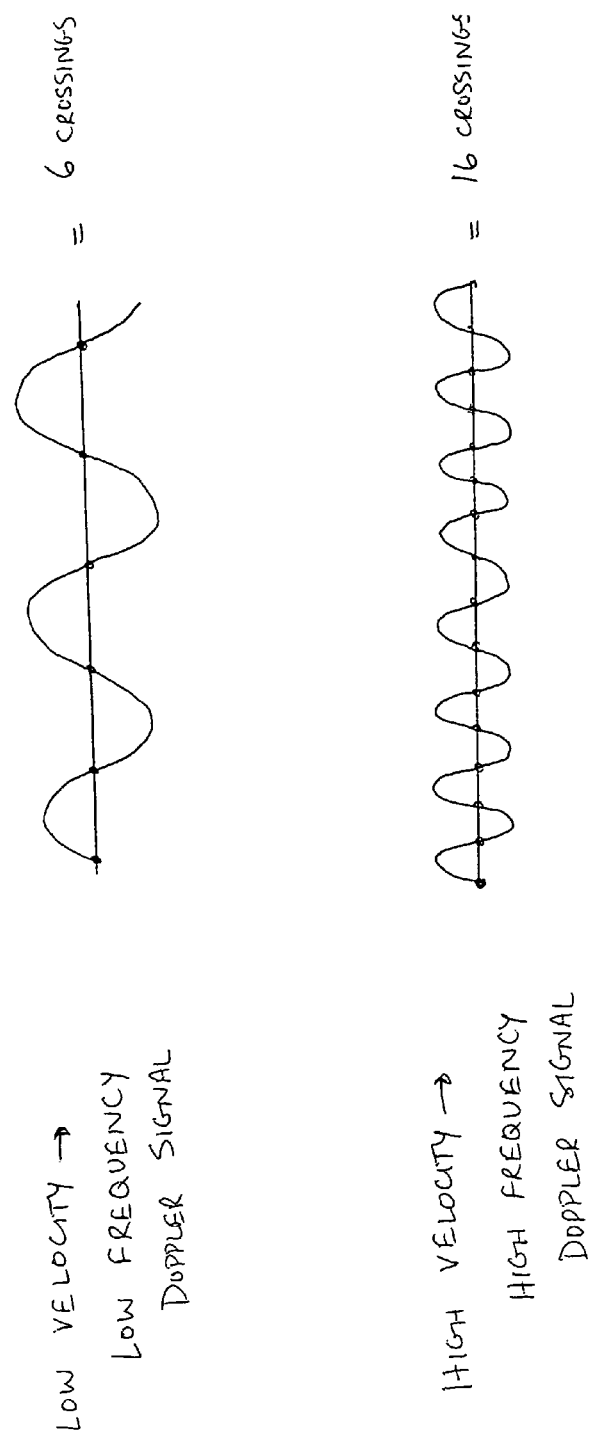
FIG. 12 is a graph illustrating "zero crossing".

In one embodiment, a flow meter and/or "signal strength meter" 54 or 55 provides for a numerical display 52, which correlates with the velocity of blood flow and/or the strength of the Doppler signal. The flow meter function is achieved by the incorporation of a "zero-crossing" detector into the transceiver circuitry. The zero-crossing detector determines the number of times a Doppler signal crosses a given threshold over a given period of time. The higher the frequency of the signal, the higher the output of the zero-crossing detector. FIG. 12 illustrates the principle upon which the zero-crossing detector generates a numerical value correlating to blood flow velocity. FIG. 13 is a block diagram representing the function of the Doppler with incorporation of the flow meter. Similar to the transceiver without a flow meter function, in one embodiment, an 8 or 20 MHz oscillator in the transceiver 50 is employed to periodically drive the ultrasonic transmitting crystal 22 located at the tip of the probe 11 or 15. The ultrasonic waves generated by the crystal 22 travel through the tissue just under the probe 11 or 15 tip in a fairly narrow beam. Waves encountering moving objects are reflected back towards the probe 11 or 15 with a frequency shift proportional to the velocity of the moving object. During the intervals when the unit is not transmitting, the crystal 22 of probe 11 or 15 receives and passes reflected signals to a receiving circuit. This circuit amplifies the returning echoes and then multiplies these received signals with the oscillator frequency (at the phase detector) to shift the returned signals into an audible range. A band pass filter then acts to reject those frequencies received at exactly 8 or 20 MHz respectively, and also those frequencies received exactly at the pulse repetition frequency. The frequencies that remain are amplified via an audio amplifier and are transmitted through the speaker of the transmitter. In addition, these frequencies are sent to the zero-crossing detector. The zero-crossing detector first converts the signal into a square wave. A frequency detector circuit within the zero-crossing detector is then used to determine the frequency of the signal over a given period of time. This generates a numerical value, which correlates with the velocity of the flow signal. This numerical value can further be converted to a modal velocity by the application of a mathematical formula (not shown). In one embodiment, a LCD display 52 is incorporated into the transceiver unit to output the numerical values generated by the zero-crossing detector. Alternative methods of displaying this quantitative output, such as printouts and CRT monitors can be employed and would be within the knowledge of one skilled in the art. The flow meter can be battery powered or A/C powered with battery powered backup capability. Though absolute blood flow values such as peak velocity can be calculated using endoscopic ultrasound coupled with color Doppler, this embodiment of the present invention provides a device that provides a relative measure or modal velocity of flow. Among its many uses, a relative measure of flow can be useful in the evaluation of esophageal varices, where flow can vary from benign levels to levels that place the patient at significant risk for bleeding episodes. In one embodiment, a flow meter 54 could be used to initially evaluate the severity of a patient's varices and could also be used post therapy to evaluate the adequacy of treatment.

Similarly, the signal strength meter function 55 is achieved by incorporating a signal strength detection circuit into the transceiver circuitry. FIG. 13 is a block diagram representing the function of the Doppler with incorporation of the signal strength meter. Similar to the transceiver without a signal strength meter function, in one embodiment, an 8 or 20 MHz oscillator in the transceiver 50 is employed to periodically drive the ultrasonic transmitting crystal 22 located at the tip of the probe 11 or 15. The ultrasonic waves generated by the crystal 22 travel through the tissue just under the probe 11 or 15 tip in a fairly narrow beam. Waves encountering moving objects are reflected back towards the probe 11 or 15 with a frequency shift proportional to the velocity of the moving object. During the intervals when the unit is not transmitting, the crystal 22 of probe 11 or 15 receives and passes reflected signals to a receiving circuit. This circuit amplifies the returning echoes at a fixed gain and then passes them through a full wave rectifier and low pass filter (collectively known as a signal strength detector) to produce a signal proportional to the audio signal strength or Doppler signal strength. In one embodiment, the LCD display 52 is used to output the numerical values generated by the signal strength meter 55. Alternative methods of displaying this quantitative output known to one skilled in the art can be employed. Two buttons 58 on the control panel 56 of the transceiver allow the user to toggle between the display of flow meter and signal strength meter readings in embodiments that incorporate both of these functions.

As mentioned above, there is often a need to identify and assess blood vessels during GI endoscopy. These vessels often lie under the tissue surface and thus cannot be visually inspected. In one embodiment of the present invention, an endoscopic Doppler system would allow for the identification and assessment of such vessels. Specific uses of such a system are outlined below.

First, an endoscopic Doppler system 10 according to one embodiment, can be used to identify blood flow in a variety of pathologies that may require haemostatic intervention. These pathologies include but are not limited to esophageal varices, esophageal ulcers, Mallory-Weiss tears, gastric varices, peptic ulcers, Dieulafoy's lesion, AVMs, and other vascular malformations. In these indications, the disposable Doppler probe 11 is passed down the endoscopic channel and is used to interrogate the tissue pathology. The presence of an audible flow signal indicates the presence of a blood vessel, thus providing the GI endoscopist with additional information upon which to base his/her treatment decision. A positive flow signal could indicate that haemostatic treatment is necessary and could also pinpoint the best location for application of that treatment. For example, in Dieulafoy's lesions, an artery aberrantly comes to the mucosal surface, often resulting in massive GI bleeding. The point at which this artery comes to the surface is often quite small (a few mm at most), and thus is difficult to detect visually during endoscopy. In addition, the artery can continue to course under, but very close to the surface, making that length of the artery susceptible to further bleeding. The endoscopic Doppler can be used to identify the artery at its point of bleeding and also its subsequent course. The physician can use this information to guide his application of haemostatic treatment such as the placement of haemoclips to occlude the vessel. Without an endoscopic Doppler, the physician has to rely on clinical judgment to guide the placement of these haemoclips.

Once a haemostatic treatment has been applied, an endoscopic Doppler system 10 can be used to assess the adequacy of the treatment. Haemostatic treatments in GI endoscopy include but are not limited to injection therapies, electrocoagulation therapies, haemoclip placement, band ligation and others. Although the GI endoscopist has several haemostatic treatments at his/her disposal, he/she does not have a means by which to assess the endpoint of treatment. That is, when a haemoclip is placed, the GI endoscopist has no way of determining whether the clip is actually occluding the blood flow (unless there is active bleeding in which case the quality of the bleeding would change). This is also true of the other currently available haemostatic treatments. Thus, there is a need for a device that allows the endoscopist to assess the effectiveness of the therapy. In one embodiment of the present invention, an endoscopic Doppler system serves this purpose.

To continue with the example of the Dieulafoy's lesion, the physician may decide to place haemoclips along the course of the flow signal. Once these clips have been placed, the endoscopist can reinsert the endoscopic Doppler probe through the endoscopic channel and re-interrogate the tissue for blood flow signals. If a persistent signal remains, the endoscopist may decide to apply further haemostatic treatment to that region. Another example would include the evaluation of esophageal varices after banding therapy. Again, if flow signals remain after banding, which can often be a random process, the endoscopist may decide to apply further treatment. In the embodiment employing a "Doppler enabled"

endoscopic instrument, detection of a flow signal and application of treatment could be achieved by a single instrument.

Finally, in one embodiment of the present invention, an endoscopic Doppler system can be used to identify "at risk" vessels prior to procedures including but not limited to sphincterotomy, polypectomy and cyst drainage, which involve incision or removal of tissue. In these procedures, the endoscopist must violate the integrity of the tissue in some fashion. This places the tissue at risk for bleeding. In some instances, an aberrant course of a significantly large artery, such as the retroduodenal artery in sphincterotomy, can lead to catastrophic bleeding requiring emergent surgery. Thus, a device, which can be used to identify blood flow signals prior to these procedures, would be clinically useful. An endoscopic Doppler system can again be passed down the endoscopic channel and used to interrogate the tissue prior to the procedure at hand. The presence of a flow signal would alert the physician to the possible need for a prophylactic haemostatic measure or the use of an alternative technique that would circumvent a bleeding complication.

In an embodiment providing a "Doppler enabled" instrument, the use of the endoscopic Doppler system 10 could be further refined. Returning back to the example of the Dieulafoy's lesion, a Doppler enabled haemoclip applier could be passed down the working channel of the endoscope to the area of interest. The Doppler mechanism of this instrument could first be used to identify the artery at its point of bleeding and trace its subsurface course. Without the need to remove the Doppler probe and insert a therapeutic instrument, the combination clip applier/Doppler could then be used to place haemoclips along the very precisely Doppler identified course of the artery. After the application of the clips, the Doppler portion of the instrument could again be used to verify that the vessel had been occluded along the entirety of its clinically relevant course. Without the need to remove and insert multiple endoscopic instruments, the physician would be able to effectively apply haemostatic treatments in precise locations and also save procedure time.

In an embodiment providing a flow meter feature 54, the uses of an endoscopic Doppler system 10 could be further refined. The flow meter 54 allows for a more objective evaluation of the flow signal. Although an audible signal can be qualitatively described as weak, strong, robust, etc., it cannot be quantified in any fashion. The incorporation of the flow meter 54 allows for quantification of the flow signal by providing a numerical output that correlates with the velocity of the blood flow. This provides the physician with an additional level of information. Such additional information could be clinically useful in a variety of endoscopic applications including but not limited to the evaluation of esophageal varices and polyps. In the instance of esophageal varices, the endoscopic Doppler flow meter would allow for the evaluation of these varices both prior to and after treatment. Currently, in cirrhotic patients who present with non-bleeding esophageal varices, a decision must be made regarding whether these lesions should be treated prophylactically. While many of these patients will not bleed, a significant portion will bleed within 1 year with high rates of morbidity and mortality. Treatment options for these patients include medical management and endoscopic band ligation. However, criteria for when patients should undergo prophylactic treatment are poorly defined. Size of the varices (which has a high degree of interobserver variability), along with other clinical parameters, is most often used to guide therapy. Objective criteria have not yet been established. Attempts have been made to correlate pressure readings (within varices or within the portal system) to the risk of variceal bleeding, but these invasive measurements have not proven to be applicable in everyday clinical practice. An endoscopic Doppler flow meter could be used to assess the relative/modal velocity of blood flow within varices. Varices with higher velocity flows may be more likely to bleed than varices with low velocities. Relative velocity could thus be used to identify patients with varices at high risk for bleeding. A non-invasive, objective measure of variceal status would prove to be a major stepping-stone in the treatment of this disease.

In an embodiment providing a signal strength meter function 55, an endoscopic Doppler system could prove to be useful in treatment of polyps. Large colonic polyps, once removed only surgically, can now be removed using an endoscopic approach. However, large polyps carry a higher risk of bleeding and it is imperative to identify those polyps that are likely to bleed after standard endoscopic techniques are used in their removal. Currently, physicians look at the size of the polyp and use their clinical judgment in deciding whether prophylactic haemostatic measures should be applied to a polyp before it is endoscopically removed. These haemostatic measures include injection of epinephrine at the base of the polyp and placement of a haemostatic loop around the stalk of a polyp. Objective criteria for the application of these measures have not yet been established. In one embodiment of the present invention, an endoscopic Doppler signal strength meter could help guide a physician in assessing the bleeding risk of a polyp. By using a Doppler signal strength meter, the physician could ascertain the strength of the Doppler signal, which would serve as a relative measure of the blood flow into a particular polyp. For example, a strong signal could identify the presence of a large vessel that may be likely to bleed with standard endoscopic "coagulate and cut" techniques. A Doppler flow meter could also be used in this situation to provide a relative measure of the velocity of blood flow into a particular polyp. Large vessels with high blood flow velocities are the most problematic vessels in terms of achieving haemostasis. Thus the presence of strong signals on the signal strength meter or of high velocities on the flow meter may serve as an objective means by which physicians could assess bleeding risk of polyps to be removed endoscopically.

As in endoscopic procedures where the endoscopist lacks tactile sensation to assess critical vasculature, the surgeon employing laparoscopic, laparoscopic-assisted or robotic-assisted techniques is also often confronted with the need to identify critical blood vessels that cannot be palpated. These vessels are often hidden, obscured by or embedded within surrounding tissue and thus cannot be found with visual inspection alone. In one embodiment of the present invention, a laparoscopic Doppler system allows for the identification and assessment of such vessels. Specific uses of this system are outlined below.

The laparoscopic Doppler system 10 can be used to identify vessels during laparoscopic radical nephrectomy or donor nephrectomy. In these procedures, the kidney is removed from the patient in its entirety. In order to achieve this, the kidney must be mobilized from all its connections within the retroperitoneal cavity, which necessitates transection of the renal vessels. Traditionally, the renal vein and artery are identified and isolated by the use of anatomical landmarks and meticulous dissection. With one embodiment of the present invention, these vessels can be more easily found. In this instance, the disposable Doppler probe 15 is passed down the laparoscopic port to interrogate the perinephric region. The presence of an audible flow signal indicates the presence of a blood vessel directly under the tip of the probe. The nature of the signal (i.e. pulsatile vs. continuous) indicates to the surgeon whether an artery or a vein has been identified. Now, the surgeon can proceed with dissection in a focused fashion, allowing for greater efficiency in the isolation of the vessel.

Not only does a laparoscopic Doppler probe aid to guide the dissection undertaken by the surgeon, but it also aids in the identification of aberrant vasculature during laparoscopic nephrectomy. Twenty-five to forty percent of kidneys present with vessels that deviate from the expected anatomical pattern. The laparoscopic Doppler probe can be used to interrogate the perinephric region to identify flow signals that would not normally be expected at certain locations. This would aid in avoiding inadvertent injury to vessels that presented in an aberrant fashion.

Another embodiment of the present invention includes use during the removal of tumors laparoscopically or with laparoscopic or robotic assistance. One example of this includes the removal of kidney tumors via partial nephrectomy. In an attempt to spare nephrons and preserve kidney function, urologists will often remove small to medium sized, localized kidney tumors by excision rather than by radical nephrectomy. In order to do this, the urologist must be able to achieve the excision with meticulous closure of the urinary collecting system and meticulous haemostatic control. Haemostatic control of the arteries, especially the major feeder artery of the tumor, is most problematic during partial nephrectomy. To minimize bleeding, urologists will often temporarily clamp the renal artery. As mentioned above, the laparoscopic Doppler can be used to facilitate the identification of the artery; the probe can then also be used to ensure that the artery has been adequately clamped. Alternatively, a laparoscopic Doppler system could be used to identify the vasculature feeding the tumor. Other instances in which such a system would be useful include but are not limited to removal of tumors via partial colectomy, hepatectomy, gastrectomy, esophagectomy, pancreatecomy, oophorectomy, hysterectomy, myomectomy, splenectomy, cystectomy, adrenalectomy, and lymphadenectomy.

A further application of the laparoscopic Doppler system includes the identification of neurovascular bundles during radical prostatectomy. Radical prostatectomy involves removal of the prostate due to malignant disease. A major complication of this procedure is impotence as the nerves controlling potency course closely to the prostate and are often damaged or removed during the procedure. A modification of radical prostatectomy is nerve sparing radical prostatectomy in which the surgeon particularly tries to spare the cavernous nerves, which are necessary for potency. However, these nerves are small and are often not easily identified during the laparoscopic procedure. Attempts have been made to facilitate the identification of these nerves. A nerve-stimulating device can be used during the procedure to help localize the nerves but this device necessitates measuring penile tumescence and has low specificity. Thus, a better device that can accurately localize the cavernous nerves is necessary.

Anatomically, the cavernous nerves course through the pelvic cavity in structures known as neurovascular bundles (NVB). The NVB incorporates both an artery and vein; these vessels are closely applied to the nerve in these bundles. Thus, identification of the neurovascular bundle can be achieved with a Doppler probe. By using the probe to identify the vascular components of the NVB, the course of the cavernous nerves is also delineated. This facilitates sparing of these structures during this procedure.

In an embodiment providing a flow meter feature 54, the uses of the laparoscopic Doppler system 10 could be further refined. The flow meter 54 allows for a more objective evaluation of the flow signal. Although an audible signal can be qualitatively described as weak, strong, robust, etc., it cannot be quantified in any fashion. In one embodiment of the present invention, the incorporation of the flow meter 54 allows for quantification of the flow signal by providing a numerical output that correlates with the velocity of the blood flow. This provides the physician with an additional level of information. To continue with the example of the sparing of the neurovascular bundle during laparoscopic nephrectomy, the Doppler flow meter could be used to assess the relative velocity of flow in the artery prior to dissection around the structure. Measurement of this value after dissection would provide the surgeon with an objective means of identifying any changes that may have occurred secondary to the dissection. A decreased or altered flow velocity might indicate damage to the neurovascular bundle. In addition, a laparoscopic Doppler flow meter could be used to more precisely evaluate feeder arteries during laparoscopic tumor resections.

Finally, in an embodiment providing a signal strength meter feature 55, a laparoscopic Doppler system would be useful during laparoscopic bowel resections and other such minimally invasive procedures. In small bowel infarction, it is critical to delineate between necrotic and viable tissue. One means of assessing this is to determine the blood flow into the tissue region. A signal strength meter could provide a numerical value correlating to the strength of the Doppler signal from each tissue region in question. Values from a Doppler flow meter would also be of use to further characterize the blood flow to a particular region of the bowel. The surgeon would then use these data points to better differentiate between viable and necrotic tissue, thus allowing for a larger segment of bowel to be spared during the resection.

One embodiment of the present invention provides a system for the detection of blood flow, that system has a transceiver unit with a signal generator having a plurality of preset signal sensitivity depth selectors such that the user can select from a variety of preset signal sensitivities so as to detect blood flow at various tissue depths. Also included is a Doppler probe for use in minimally invasive applications coupled to the transceiver. The Doppler probe provides a piezoelectric crystal disposed at a first end of the Doppler probe, and at least one wire transmitting signals between the transceiver unit and the piezoelectric crystal. The system also provides a transceiver unit coupler disposed at a second end of said Doppler probe.

In some embodiments, the system may be portable or provide a disposable probe. While in others, the system may also provide a quantitative blood flow meter. The quantitative blood flow meter may have a numeric display.

Such a quantitative flow meter may be provided with a graphic display. In one embodiment, the graphic display provides a paper printout.

Various embodiments of the present invention provide a sheath disposed around at least part of the at least one wire and the piezoelectric crystal. This sheath may be either rigid or flexible. Such a sheath may be a surgical instrument or may be provided with at least one channel disposed within the sheath. In the latter instance, a surgical instrument may disposed within said at least one channel. Alternatively, the channel may be coupled to a tissue marking dye source whereby a tissue marking dye may be delivered to the first end of the Doppler probe. Similarly, the channel may be coupled to a vacuum source, and whereby a vacuum may be applied to a target, steadying the Doppler probe proximate to said target. Alternatively, channel may be coupled to at least one electrically activated adhesive pad.

One embodiment of the system may also provide a signal strength meter.

Another embodiment of the present invention provides a method for the assessment of blood flow in vessels, that method being: inserting a Doppler probe into a body cavity; positioning said Doppler probe proximate to a target tissue region; selecting a depth of signal sensitivity from a plurality of preset signal depths; emitting at least one pulse from the Doppler probe; receiving at least one reflected pulse; generating an audio signal correlating to the velocity of blood flowing in the vessel; and assessing blood flow in the vessel based on the audio signal.

In other embodiments, the step of inserting a Doppler probe into a body cavity may include a step selected from the group of steps consisting of inserting said Doppler probe via an endoscopic channel of an endoscope, and inserting said Doppler probe via a laparoscopic port. The method may also include providing a quantitative measure correlating to velocity of the blood flowing in the vessel. Alternative embodiments of the method employ assessment of blood flow in at least one medical procedure, selected from the group of medical procedures consisting of assessment of esophageal varices, esophageal ulcers, Mallory-Weiss tears, gastric varices, Dieulafoy's lesion, AVMs, vascular malformations, post-haemostatic treatment assessment, and pre-operative assessment of incision sights for sphincterotomy, polypectomy and cyst drainage. Alternatively, assessment of blood flow may be employed in at least one medical procedure, selected from the group of medical procedures consisting of partial and total nephrectomy, prostatectomy with nerve sparing, pyeloplasty, varicocelectomy, adrenalectomy, lymph node dissection, tumor resection and resection of small bowel for infarction.

Other embodiments of the invention may monitor signal strength with a signal strength meter.

Another embodiment of the present invention provides a system for the quantitative assessment of blood flow, the system having a transceiver unit with a signal generator, a signal comparator, and an audio output whereby a user receives an audio signal indicating differences in Doppler signal. A Doppler probe is coupled to the transceiver. A flow meter is provided that provides a visual quantitative display and a zero-crossing detector. The Doppler probe of one embodiment of the present invention has a piezoelectric crystal disposed at a first end of the Doppler probe; at least one wire transmitting signals between the transceiver unit to the piezoelectric crystal; a sheath disposed around at least part of the at least one wire and the piezoelectric crystal; a transceiver unit coupler disposed at a second end of the Doppler probe.

Such a system may, in some embodiments have a plurality of preset signal sensitivity depth selectors.

Other embodiments of the present invention provide a system for the quantitative assessment of blood flow, that system having a transceiver unit comprising a signal generator, a signal comparator, and an audio output whereby a user receives an audio signal indicating differences in Doppler signal and a Doppler probe coupled to said transceiver. According to such an embodiment, a signal strength meter comprising a visual quantitative display and a signal strength detector may be provided. The Doppler probe may include a piezoelectric crystal disposed at a first end of the Doppler probe. At least one wire is included transmitting signals between the transceiver unit to the piezoelectric crystal. In some such embodiments, a sheath is disposed around at least part of the wire and piezoelectric crystal. A transceiver unit coupler may be disposed at a second end of the Doppler probe. In some embodiments a plurality of preset signal sensitivity depth selectors is provided.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A system for the detection of blood flow, the system comprising:
    a non-imaging Doppler transceiver unit comprising a signal generator having a plurality of factory defined preset signal sensitivity depth selectors, said preset signal sensitivity depth selectors being configured to allow a user to transition between standard signal depths during a procedure;
    a Doppler probe for insertion in to a body cavity, said cavity being external to a target blood vessel during minimally invasive surgical procedures coupled to said transceiver; said Doppler probe comprising;
    a piezoelectric crystal disposed at a first end of said Doppler probe;
    at least one wire transmitting signals between said transceiver unit to said piezoelectric crystal and a transceiver unit coupler disposed at a second end of said Doppler probe.

2. The system according to claim 1 wherein said transceiver is portable.

3. The system according to claim 1 wherein said probe is disposable.

4. The system according to claim 1 further comprising a quantitative blood flow meter.

5. The system according to claim 4 wherein said blood flow meter comprises a numeric display.

6. The system according to claim 4 wherein said meter comprises a graphic display.

7. The system according to claim 6 wherein said graphic display comprises a paper printout.

8. The system according to claim 1 further comprising a signal strength meter having an amplifier for amplifying reflected signals, a rectifier for rectifying said reflected signal and a low band filter producing a signal proportional to said reflected signal strength.

9. The system according to claim 1 further comprising a sheath disposed around at least part of said at least one wire and said piezoelectric crystal.

10. The system according to claim 9 wherein said sheath is rigid.

11. The system according to claim 9 wherein said sheath is flexible.

12. The system according to claim 9 wherein said sheath comprises a surgical instrument.

13. The system according to claim 9 further comprising at least one channel disposed within said sheath.

14. The system according to claim 13 further comprising at least one surgical instrument disposed within said at least one channel.

15. The system according to claim 13 wherein at least one said channel is coupled to a tissue marking dye source, and whereby a tissue marking dye may be delivered to said first end of said Doppler probe.

16. The system according to claim 13 wherein at least one said channel is coupled to a vacuum source, and whereby a vacuum may be applied to a target, steadying said Doppler probe proximate to said target.

17. The system according to claim 13 wherein at least one said channel is coupled to at least one electrically activated adhesive pad.

18. A method for the assessment of blood flow in vessels, said method comprising:
    inserting a Doppler probe into a body cavity external to a blood vessel;
    positioning said Doppler probe proximate to a target tissue region;
    selecting a depth of signal sensitivity from a plurality of factory defined preset signal depths configured for transition during a procedure;
    emitting at least one pulse from said Doppler probe;
    receiving at least one reflected pulse;
    generating an audio signal correlating to the velocity of blood flowing in said vessel; and
    assessing blood flow in said vessel based on said audio signal and without an ultrasonic image.

19. The method according to claim 18 wherein said step of inserting a Doppler probe into a body cavity comprises a step selected from the group of steps consisting of inserting said Doppler probe via an endoscopic channel of an endoscope, and inserting said Doppler probe via a laparoscopic port.

20. The method according to claim 18 further comprising providing a quantitative measure correlating to velocity of said blood flowing in said vessel.

21. The method according to claim 18 wherein said assessment of blood flow is employed in at least one medical procedure, selected from the group of medical procedures consisting of assessment of esophageal varices, esophageal ulcers, Mallory-Weiss tears, gastric varices, Dieulafoy's lesion, AVMs, vascular malformations, post-haemostatic treatment assessment, and pre-operative assessment of incision sights for sphincterotomy, polypectomy and cyst drainage.

22. The method according to claim 18 wherein said assessment of blood flow is employed in at least one medical procedure, selected from the group of medical procedures consisting of partial and total nephrectomy, prostatectomy with nerve sparing, pyeloplasty, varicocelectomy, adrenalectomy, lymph node dissection, tumor resection and resection of small bowel for infarction.

23. The method according to claim 18 further comprising monitoring signal strength by amplifying returning echoes at a fixed gain and then passes them through a full wave rectifier and low pass filter.

24. A system for the quantitative assessment of blood flow, said system comprising:
    a non-imaging Doppler transceiver unit comprising a signal generator, a signal comparator, and an audio output whereby a user receives an audio signal indicating differences in Doppler signal;
    a Doppler probe coupled to said transceiver; and
    a flow meter comprising a visual quantitative display and a zero-crossing detector;
    said Doppler probe comprising:
    a piezoelectric crystal disposed at a first end of said Doppler probe;
    at least one wire transmitting signals between said transceiver unit to said piezoelectric crystal;
    a sheath disposed around at least part of said at least one wire and said piezoelectric crystal;
    a transceiver unit coupler disposed at a second end of said Doppler probe; and
    a plurality of factory defined preset signal sensitivity depth selectors.

25. A system for the quantitative assessment of blood flow, said system comprising:
    a non-imaging, Doppler transceiver unit comprising a signal generator, a signal comparator, and an audio output whereby a user receives an audio signal indicating differences in Doppler signal;
    a Doppler probe coupled to said transceiver; and
    a signal strength meter comprising a visual quantitative display and a signal strength detector having an amplifier for amplifying a reflected signal, a rectifier for rectifying said reflected signal and a low band filter producing a signal proportional to strength of said reflected signal;
    said Doppler probe comprising:
    a piezoelectric crystal disposed at a first end of said Doppler probe;
    at least one wire transmitting signals between said transceiver unit to said piezoelectric crystal;
    a sheath disposed around at least part of said at least one wire and said piezoelectric crystal
    a transceiver unit coupler disposed at a second end of said Doppler probe; and
    a plurality of factory preset signal sensitivity depth selectors.

* * * * *